(12) United States Patent
Soo et al.

(10) Patent No.: US 9,730,965 B2
(45) Date of Patent: Aug. 15, 2017

(54) PERIVASCULAR STEM CELL COMPOSITION FOR BONE

(75) Inventors: B. Chia Soo, Beverly Hills, CA (US); Kang Ting, Beverly Hills, CA (US); Bruno Peault, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/371,330

(22) Filed: Feb. 10, 2012

(65) Prior Publication Data
US 2012/0244128 A1    Sep. 27, 2012

Related U.S. Application Data

(63) Continuation of application No. PCT/US2010/002297, filed on Aug. 20, 2010.

(60) Provisional application No. 61/235,618, filed on Aug. 20, 2009.

(51) Int. Cl.
A61K 35/44 (2015.01)
A61K 38/17 (2006.01)

(52) U.S. Cl.
CPC .......... *A61K 35/44* (2013.01); *A61K 38/1709* (2013.01)

(58) Field of Classification Search
CPC ............... A61K 35/44; A61K 38/1709; C12N 2501/155
USPC ................................................. 424/93.7, 484
See application file for complete search history.

(56) References Cited

U.S. PATENT DOCUMENTS

| | | | |
|---|---|---|---|
| 7,413,734 B2 * | 8/2008 | Mistry et al. | 424/93.7 |
| 7,833,968 B2 * | 11/2010 | Soo et al. | 514/16.9 |
| 8,053,412 B2 * | 11/2011 | Ting et al. | 514/16.7 |
| 2006/0193840 A1 | 8/2006 | Gronthos et al. | |
| 2006/0292670 A1 | 12/2006 | Ting et al. | |
| 2007/0056595 A1 | 3/2007 | McLachlan | |
| 2007/0264239 A1 | 11/2007 | Huard et al. | |
| 2007/0264306 A1 | 11/2007 | Flameng et al. | |
| 2009/0087415 A1 | 4/2009 | Culiat | |
| 2009/0191632 A1 | 7/2009 | Fadeev et al. | |
| 2011/0111030 A1 * | 5/2011 | Bhasin | 424/484 |
| 2012/0077742 A1 * | 3/2012 | Ting et al. | 514/8.1 |
| 2012/0244128 A1 | 9/2012 | Soo et al. | |

OTHER PUBLICATIONS

Crisan et al., A perivascular origin for mesenchymal stem cells in multiple human organs. Cell Stem Cell, vol. 3 (Sep. 11, 2008) pp. 301-313.*

Kalajzic et al., "Use of an alpha-smooth muscle actin (SMAA) GFP reporter to identify an osteoprogenitor population", Bone 43(3), pp. 501-510 (2008).

Lin et al., 2008, "Defining Stem and Progenitor Cells within Adipose Tissue," *Stem Cells and Development* 17: 1053-1064.

* cited by examiner

*Primary Examiner* — Kara Johnson
(74) *Attorney, Agent, or Firm* — Duane Morris LLP

(57) ABSTRACT

Embodiments of the present invention provide an osteogenic composition comprising perivascular stem cells or induced pluripotent cells (iPS) and an osteogenic agent and methods of making and using the same.

20 Claims, 16 Drawing Sheets

PERIVASCULAR STEM CELL COMPOSITION FOR BONE

CROSS-REFERENCE TO RELATED APPLICATIONS

This application is a continuation of PCT/US2010/002297, filed on Aug. 20, 2010, which claims the benefit of U.S. provisional application No. 61/235,618, filed on Aug. 10, 2009. The teaching in these applications is incorporated hereto in its entirety by reference.

TECHNICAL FIELD OF THE INVENTION

The present invention generally relates to perivascular stem cells (PSC) or induced pluripotent stem cells (iPS) for bone and methods of making and using the same.

BACKGROUND OF THE INVENTION

Bone grafts are used worldwide to treat musculoskeletal defects in millions of orthopaedic, neurocranial, plastic, and oral/dental surgeries each year [1]. The gold standard bone graft material is autograft bone. However, besides limited supply, prolonged surgery time and increased blood loss, autograft bone harvest is associated with many donor site morbidities including pain, gait disturbance, thigh paresthesia for iliac crest donor sites, and infection, neurologic deficits, and hematomas for calvarial donor sites. In addition, aging and osteoporosis reduce stem cell availability and activity in the bone marrow, creating an unfavorable microenvironment that promotes adipogenesis over osteogenesis [2], [3], which may account for failed fracture healing in up to 50% of osteoporotic patients [4]. Thus, for patients with poor quality bone, iliac bone harvest can lead to severe complications such as iliac crest fracture and complete pelvic ring failure [5]. On top of this, any bone harvested from osteoporotic patients can contain the same suboptimal microenvironment and diminished repair capacity [6]. Overall, autograft bone use is complicated by limited supply, significant harvest morbidities, and inconsistent bone regeneration properties.

Current autologous bone graft substitutes have undesirable side effects or lower efficacy. The most effective bone graft substitute in use is BMP2 (INFUSE® Bone Graft) [7]. BMP2, however, has elicited life-threatening cervical swelling [8], osteoclast activation [9], adipogenic differentiation [2], bone cyst formation [10,11], and tumor growth [12]. Newer combinations of cryopreserved allogeneic mesenchymal stem cells and allograft cancellous bone [e.g. Osteocel®, Trinity® Evolution™ (TE®)] involve processing steps that remove immunogenic components but also deplete osteogenic cells and osteoinductive factors—making these products less effective (unpublished data). Thus, there is an urgent need for safer and more effective bone graft substitutes that retain high efficacy even in suboptimal micro environments.

While many current bone graft substitutes promote various degrees of osteogenesis, few provide adequate numbers of the appropriate stem cells, and none provide factors that concomitantly promote osteogenesis while inhibiting adipogenesis [13].

Stem cells can accelerate bone regeneration by promoting osteoprogenitors and improve vascular ingrowth [14]. Current conventional stem cell sources, however, have significant drawbacks. Low stem cell numbers/high donor site morbidity limit the use of fresh autologous bone marrow [15,16], while the need for culture and long derivation times hamper the use of bone marrow stem cells (BMSC) or adipose derived stem cells (ASC). Culturing also introduces immunogenicity, infection, and genetic instability/potential tumorigenicity risks [17,18]. In addition, significant cell heterogeneity, including high numbers of non stem cells, non viable cells, and the presence of differentiation inhibiting endothelial cells [19,20] may decrease the osteogenic efficacy of adipose total stromal vascular fractions.

The embodiments described below address the above identified problems and needs.

SUMMARY OF THE INVENTION

In an aspect of the present invention, it is provided an osteogenic composition, comprising a population of perivascular stem cells (PSC) or induced pluripotent stem cells (iPS) and an osteoinductive agent. The osteoindutive agent can be a chemical or protein agent in a therapeutically effective amount for causing PSC or iPS to differentiate in the osteoblast or progenitor lineages so as to generate a bone tissue. Alternatively, the osteoinductive agent can be a chemical or protein agent in a therapeutically effective amount for enhancing the survivability or engraftment of the PSC or iPS where PSC or iPS provide trophic factors or enhance vascular ingrowth so as to treat, delay, or ameliorate a bone condition.

In some embodiments, the osteoinductive agent is a NELL-1 factor, which can be a NELL-1 protein. The NELL-1 protein is in a therapeutically effective amount in the composition, which upon delivery, is effective for causing PSC or iPS to differentiate in the osteoblast or progenitor lineages so as to generate a bone tissue. Alternatively, the NELL-1 protein is in a therapeutically effective amount for enhancing the survivability or engraftment of the PSC or iPS where PSC or iPS provide trophic factors or enhance vascular ingrowth so as to treat, delay, or ameliorate a bone condition.

The PSC can be human PSC or animal PSC, and can be autologous PSC, allograft PSC, or xenograft PSC. The iPS can be human iPS or animal iPS, and can be autologous iPS, allograft iPS, or xenograft iPS. The PSC or iPS can have a density from about $1\times10^4$ to about $1\times10^8$/mL (per 1 mL volume of the composition). In some embodiments, the seeding density can be from about $1\times10^4$ to about $1\times10^6$, from about $1\times10^4$ to about $1\times10^5$, from about $1\times10^5$ to about $1\times10^7$, from about $1\times10^5$ to about $1\times10^6$, from about $1\times10^6$ to about $1\times10^7$/ml, or from about $1\times10^7$ to about $1\times10^8$/ml. Examples of seeding densities can be, e.g., $0.5\times10^4$, $1\times10^4$, $0.5\times10^5$, $1\times10^5$, $0.5\times10^6$, $1\times10^6$, $0.5\times10^7$, $1\times10^7$, or $1\times10^8$/ml.

In some embodiments, the term PSC can be pericytes or adventitia cells. In some embodiments, iPS can be used in place of PSC in the various embodiments of invention disclosed herein.

The composition can be formulated into different formulations. In some embodiments, the composition can be an osteogenic implant. Such an implant can be, for example, a spine fusion implant. In some embodiments, the composition can comprise an osteogenic scaffold wherein the scaffold comprises NELL-1 as an osteoinductive agent to cause the PSC or iPS to differentiate into osteoblasts or osteoprogenitor cells or to enhance the survivability or engraftment of the PSC or iPS where PSC or iPS provide trophic factors or enhance vascular ingrowth so as to treat, delay, or ameliorate a bone condition.

In some embodiments, the composition can further comprise an excipient. Such an excipient can be, e.g., a pharmaceutically acceptable carrier, which is further described below.

In another aspect of the present invention, it is provided a method of fabricating a composition for bone regeneration, the method comprising:
providing an osteoinductive agent,
providing a population of perivascular stem cells (PSC) or induced pluripotent stem cells (iPS), and
forming the composition.

In the method, the osteoinductive agent can be a chemical agent or a biological agent. The osteoindutive agent can be a chemical or protein agent in a therapeutically effective amount for causing PSC or iPS to differentiate in the osteoblast or progenitor lineages so as to generate a bone tissue. Alternatively, the osteoinductive agent can be a chemical or protein agent in a therapeutically effective amount for enhancing the survivability or engraftment of the PSC or iPS where PSC or iPS provide trophic factors or enhance vascular ingrowth so as to treat, delay, or ameliorate a bone condition.

The PSC can be human PSC or animal PSC, and can be autologous PSC, allograft PSC, or xenograft PSC. The iPS can be human iPS or animal iPS, and can be autologous iPS, allograft iPS, or xenograft iPS. The PSC or iPS can have a density from about $1\times10^4$ to about $1\times10^8$/mL (per 1 mL volume of the composition). In some embodiments, the seeding density can be from about $1\times10^4$ to about $1\times10^6$, from about $1\times10^4$ to about $1\times10^5$, from about $1\times10^5$ to about $1\times10^7$, from about $1\times10^5$ to about $1\times10^6$, from about $1\times10^6$ to about $1\times10^7$/ml, or from about $1\times10^7$ to about $1\times10^8$/ml. Examples of seeding densities can be, e.g., $0.5\times10^4$, $1\times10^4$, $0.5\times10^5$, $1\times10^5$, $0.5\times10^6$, $1\times10^6$, $0.5\times10^7$, $1\times10^7$, or $1\times10^8$/ml.

In some embodiments, the term PSC can be pericytes or adventitia cells. In some embodiments, iPS can be used in place of PSC in the various embodiments of invention disclosed herein.

In some embodiments of the method, the composition can be formulated into different formulations. In some embodiments, the composition can be an osteogenic implant. Such an implant can be, for example, a spine fusion implant. In some embodiments, the composition can comprise an osteogenic scaffold wherein the scaffold comprises NELL-1 as an osteoinductive agent to cause the PSC or iPS to differentiate into osteoblasts or osteoprogenitor cells or to enhance the survivability or engraftment of the PSC or iPS where PSC or iPS provide trophic factors or enhance vascular ingrowth so as to treat, delay, or ameliorate a bone condition.

In some embodiments of the method, the composition can further comprise an excipient. Such an excipient can be, e.g., a pharmaceutically acceptable carrier, which is further described below.

In another aspect of the present invention, it is provided a method of treating or ameliorating a bone condition, comprising administering to a subject a composition according to the various embodiments above. The bone condition can be any bone condition where bone regeneration is desired. In some embodiments, the bone condition is a spine condition. In some embodiments, the bone condition is osteoporosis.

DETAILED DESCRIPTION OF THE INVENTION

Figure 1:
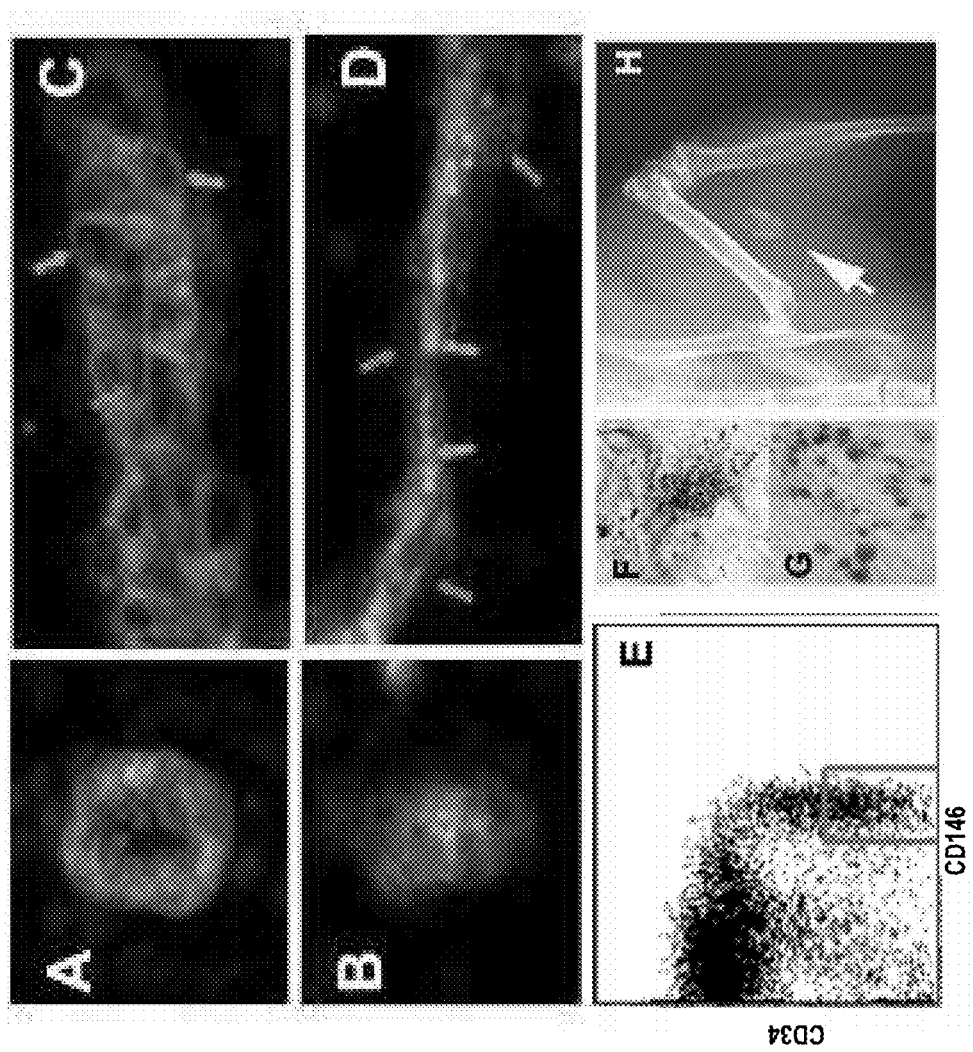
FIGS. 1A-1H show pericytic MSC. All human pericytes express CD146 (A, green; endothelial CD34 is red; B, red; CD34 is green), NG2 (C, green; endothelial VE-cadherin is red) and PDGF-Rβ (D, red; endothelial von Willebrand factor (vWF) is green). E: Pericytes are purified by fluorescence activated cell sorting (FACS) as CD45–CD56–CD146+CD34– cells (red gate). Pericytes cultivated in osteogenic medium for 21 days: F, von Kossa staining; mineral deposits appear in black. G, alizarin red staining; calcium deposits are stained red. H: Pericytes embedded in a Gelfoam sponge in the presence of BMP2 were implanted in a SCID-NOD mouse muscle pocket. X-ray analysis at day 30 after implantation.

In an aspect of the present invention, it is provided an osteogenic composition, comprising a population of perivascular stem cells (PSC) or induced pluripotent stem cells (iPS) and an osteoinductive agent. The osteoindutive agent can be a chemical or protein agent in a therapeutically effective amount for causing PSC or iPS to differentiate in the osteoblast or progenitor lineages so as to generate a bone tissue. Alternatively, the osteoinductive agent can be a chemical or protein agent in a therapeutically effective amount for enhancing the survivability or engraftment of the PSC or iPS where PSC or iPS provide trophic factors or enhance vascular ingrowth so as to treat, delay, or ameliorate a bone condition.

In some embodiments, the osteoinductive agent is a NELL-1 factor, which can be a NELL-1 protein. The NELL-1 protein is in a therapeutically effective amount in the composition, which upon delivery, is effective for causing PSC or iPS to differentiate in the osteoblast or progenitor lineages so as to generate a bone tissue. Alternatively, the NELL-1 protein is in a therapeutically effective amount for enhancing the survivability or engraftment of the PSC or iPS where PSC or iPS provide trophic factors or enhance vascular ingrowth so as to treat, delay, or ameliorate a bone condition.

The PSC can be human PSC or animal PSC, and can be autologous PSC, allograft PSC, or xenograft PSC. The iPS can be human iPS or animal iPS, and can be autologous iPS, allograft iPS, or xenograft iPS. The PSC or iPS can have a density from about $1 \times 10^4$ to about $1 \times 10^8$/mL (per 1 mL volume of the composition). In some embodiments, the seeding density can be from about $1 \times 10^4$ to about $1 \times 10^6$, from about $1 \times 10^4$ to about $1 \times 10^5$, from about $1 \times 10^5$ to about $1 \times 10^7$, from about $1 \times 10^5$ to about $1 \times 10^6$, from about $1 \times 10^6$ to about $1 \times 10^7$/ml, or from about $1 \times 10^7$ to about $1 \times 10^8$/ml. Examples of seeding densities can be, e.g., $0.5 \times 10^4$, $1 \times 10^4$, $0.5 \times 10^5$, $1 \times 10^5$, $0.5 \times 10^6$, $1 \times 10^6$, $0.5 \times 10^7$, $1 \times 10^7$, or $1 \times 10^8$/ml.

In some embodiments, the term PSC can be pericytes or adventitia cells. In some embodiments, iPS can be used in place of PSC in the various embodiments of invention disclosed herein.

The composition can be formulated into different formulations. In some embodiments, the composition can be an osteogenic implant. Such an implant can be, for example, a spine fusion implant. In some embodiments, the composition can comprise an osteogenic scaffold wherein the scaffold comprises NELL-1 as an osteoinductive agent to cause the PSC or iPS to differentiate into osteoblasts or osteoprogenitor cells or to enhance the survivability or engraftment of the PSC or iPS where PSC or iPS provide trophic factors or enhance vascular ingrowth so as to treat, delay, or ameliorate a bone condition.

In some embodiments, the composition can further comprise an excipient. Such an excipient can be, e.g., a pharmaceutically acceptable carrier, which is further described below.

In another aspect of the present invention, it is provided a method of fabricating a composition for bone regeneration, the method comprising:
providing an osteoinductive agent,
providing a population of perivascular stem cells (PSC) or induced pluripotent stem cells (iPS), and
forming the composition.

In the method, the osteoinductive agent can be a chemical agent or a biological agent. The osteoindutive agent can be a chemical or protein agent in a therapeutically effective amount for causing PSC or iPS to differentiate in the osteoblast or progenitor lineages so as to generate a bone tissue. Alternatively, the osteoinductive agent can be a chemical or protein agent in a therapeutically effective amount for enhancing the survivability or engraftment of the PSC or iPS where PSC or iPS provide trophic factors or enhance vascular ingrowth so as to treat, delay, or ameliorate a bone condition.

The PSC can be human PSC or animal PSC, and can be autologous PSC, allograft PSC, or xenograft PSC. The iPS can be human iPS or animal iPS, and can be autologous iPS, allograft iPS, or xenograft iPS. The PSC or iPS can have a density from about $1 \times 10^4$ to about $1 \times 10^8$/mL (per 1 mL volume of the composition). In some embodiments, the seeding density can be from about $1 \times 10^4$ to about $1 \times 10^6$, from about $1 \times 10^4$ to about $1 \times 10^5$, from about $1 \times 10^5$ to about $1 \times 10^7$, from about $1 \times 10^5$ to about $1 \times 10^6$, from about $1 \times 10^6$ to about $1 \times 10^7$/ml, or from about $1 \times 10^7$ to about $1 \times 10^8$/ml. Examples of seeding densities can be, e.g., $0.5 \times 10^4$, $1 \times 10^4$, $0.5 \times 10^5$, $1 \times 10^5$, $0.5 \times 10^6$, $1 \times 10^6$, $0.5 \times 10^7$, $1 \times 10^7$, or $1 \times 10^8$/ml.

In some embodiments, the term PSC can be pericytes or adventitia cells. In some embodiments, iPS can be used in place of PSC in the various embodiments of invention disclosed herein.

In some embodiments of the method, the composition can be formulated into different formulations. In some embodiments, the composition can be an osteogenic implant. Such an implant can be, for example, a spine fusion implant. In some embodiments, the composition can comprise an osteogenic scaffold wherein the scaffold comprises NELL-1 as an osteoinductive agent to cause the PSC or iPS to differentiate into osteoblasts or osteoprogenitor cells or to enhance the survivability or engraftment of the PSC or iPS where PSC or iPS provide trophic factors or enhance vascular ingrowth so as to treat, delay, or ameliorate a bone condition.

In some embodiments of the method, the composition can further comprise an excipient. Such an excipient can be, e.g., a pharmaceutically acceptable carrier, which is further described below.

In another aspect of the present invention, it is provided a method of treating or ameliorating a bone condition, comprising administering to a subject a composition according to the various embodiments above. The bone condition can be any bone condition where bone regeneration is desired. In some embodiments, the bone condition is a spine condition. In some embodiments, the bone condition is osteoporosis.

As used herein, the terms "NELL-1 protein", "NELL-1 peptide", and "NELL-1 factor" are sometimes used interchangeably.

As used herein, the term "osteoinductive agent" is a chemical or biological agent effective for stimulating vascular ingrowth or bone growth. Alternatively, the term "osteoinductive agent" refers to a chemical or biological agent effective for enhancing the survivability or engraftment of the PSC or iPS where PSC or iPS provide trophic factors or enhance vascular ingrowth. In some embodiments, the osteoinductive agent is a NELL-1 factor. In some other embodiments, the osteoinductive agent can be any of bone morphogenetic proteins (BMPs), vascular epithelial growth factor (VEGF), platelet derived growth factor (PDGF), osteogenic peptides, angiogenic peptides, and combinations thereof.

As used herein, the term "therapeutically effective amount" means the dose of a osteoinductive agent (e.g., a NELL-1 factor) required to cause a PSC or iPS to differentiate into a osteoblast or progenitor cell to achieve bone tissue regeneration so as to treat, delay, or ameliorate a bone condition. Alternatively, the term "therapeutically effective amount" means the dose of a osteoioinductive agent (e.g., a NELL-1 factor) required for enhancing the survivability or engraftment of the PSC or iPS where PSC or iPS provide trophic factors or enhance vascular ingrowth so as to treat, delay, or ameliorate a bone condition.

Cell-Based Bone Regeneration

Cell-free approaches using biocompatible scaffolds and bioactive factors rely on recruiting endogenous, local cells for bone formation. Application of rhBMP2 (INFUSE® Bone Graft) or platelet-derived growth factor (GEM21S®) are examples of this cell-free approach. However, for large defects that exceed the regenerative capacity of local osteoprogenitors or in patients with diminished osteoprogenitor reserve or locally compromised tissues (e.g., avascular scar), cell-based approaches to introduce osteoprogenitors and improve vascular ingrowth can significantly enhance bone regeneration efficacy. In support of this, adipose-derived stem cells (ASC) expressing BMP2 exhibited significantly more bone growth than high dose rhBMP2 alone in a rat spine fusion model [21]. In addition, over 300 papers document the efficacy of using cell-based bone tissue engineering (reviewed in [22])

Appropriately differentiated human stem cells can significantly augment bone regeneration [23]. The rationale for using adult autologous perivascular stem cells (PSC) rather than human embryonic stem cells (hESC) is that while hESC hold great promise for regenerative medicine, obstacles such as prolonged exposure to animal products in culture medium, teratoma formation, and potential need for immunosuppression remain significant safety issues to clinical hESC use [24,25].

The benefits of adipose-derived PSC use over autograft bone include i) minimal morbidity from suction-assisted lipectomy and ii) more abundant stem cell supply. Approximately 100 ml of fat tissue can yield in excess of $1\times10^6$ stem cells, while a typical bone marrow aspirate of 40 ml yields $\sim2.5\times10^4$ stem cells in a mature adult [15]. Also, bone marrow harvests >40-50 ml are generally limited by donor site morbidity, while average liposuction volumes are well over 1 L [15,26,27]. Thus, bone marrow derived stem cells typically require ex vivo expansion to achieve adequate therapeutic cell dosing [16]. In contrast easily accessible, available and dispensable adipose tissues can yield sufficient stem cells without ex vivo cell expansion.

Frozen bone-substitute products containing allogeneic marrow-derived cells are available commercially (e.g., Trinity® Evolution™, Orthofix; Osteocel®; Nuvasive). These are classified by the FDA as Human Cells, Tissues and Cellular and Tissue-Based Products (HCT/P) and did not require premarket review [7]. Thus, there is no formal safety or efficacy data on these products. To meet the HCT/P criteria, these cellular bone substitute products were processed with "minimal manipulation" from allogeneic bone tissues. Since bone tissues are naturally low in mesenchymal stem cells, declining to 1 in every 250,000 cells by 30 years of age [28], the number of marrow stem cells available for bone regeneration is correspondingly low. Meanwhile, processing and freezing can further decrease stem cell viability. In support of this, our data (see data in the Examples, below) comparing cellular bone substitute products alone or cellular bone substitute products with PSC, demonstrated more bone formation when PSC are present.

The majority of cell expansion or culturing procedures are based on the use of fetal bovine serum (FBS), which carries the risk of xenoimmunization [e.g., nonhuman immunogenic sialic acid (Neu5Gc)] and transmission of known (e.g, prions transmitting bovine spongiform encephalopathy) and unknown pathogens [17]. Also, irrespective of culture medium, ex vivo culture increases the risk of microbiological or particulate contamination [17] as well as genetic instability [18]. From a safety standpoint, the use of freshly harvested and sorted PSC is superior to that of cultured MSC such as ASC because it decreases immunogenic, infectious, and tumorigenic risks.

Other advantages of PSC use over MSC are: 1] precise characterization in terms of native tissue localization, phenotype and developmental potential, (MSC are retrospectively derived from primary, heterogeneous cell cultures) and 2] improved trophic potency (we have determined that PSC secrete 10-20 times more heparin binding epidermal growth factor and 3-7 times more basic fibroblast growth factor and vascular endothelial growth factor than classically derived adipose tissue and cord blood MSC [29]. Thus from an FDA regulatory perspective using PSC can facilitate demonstration of product identity, purity, sterility, safety, and potency.

Although the majority of cell-based bone regeneration studies have used cultured ASC rather than freshly harvested stromal vascular fraction (SVF) [30] from adipose tissue, using SVF would remove the need for ex vivo culture and significantly simplify cell-based bone repair. However, available studies using SVF show decreased bone regeneration efficacy relative to cultured ASC [31,32,33].

One explanation for this is that freshly harvested SVF cells from adipose tissues are a heterogeneous population that includes preadipocytes, endothelial and other vascular cells, macrophages, leukocytes, fibroblasts and adipose-derived stem cells (ASC) that share several characteristics with BMSC [34,35]. In this regard, there is documented evidence that endothelial cells present in SVF negatively regulate the differentiation potential of MSC such as ASC or BMSC [19,20]. For instance, human endothelial cells inhibit BMSC differentiation into mature osteoblasts by interfering with Osterix expression, a gene critical for osteoblastic differentiation [20], while endothelial cells inhibited adipogenic differentiation of ASC [19]. Thus, endothelial cells in SVF apparently inhibit osteoblastic differentiation of ACS.

Using immunohistochemistry and flow cytometry (FACS), two distinct perivascular cell populations can be obtained: microvessel pericytes (CD146+, NG2+, PDGF-Rβ+, CD34−, CD45−) [36] and adventitial cells (CD146−, NG2−, PDGF-Rβ−, CD34+, CD45−, CD31−), and these cells, freshly isolated or cultured long term, are indistinguishable from classic MSC—hence they were termed collectively perivascular stem cells or PSC. Importantly, a PSC purification protocol that enables the isolation of all multipotent stem cell populations, free of endothelial cells, from all human tissues tested thus far has been developed (Peault, et al., submitted for publication).

When cultured in osteogenic medium, PSC express alkaline phosphatase and mineralize. Human PSC transplanted intramuscularly with BMP2 in immunodeficient mice develop into bone [36]. In addition, freshly harvested PSC and cultured PSC regenerated muscle with similar efficacy, indicating that, at least with respect to PSC, there is no inherent advantage to pre-implantation ex vivo culture [36]. Thus, unlike freshly harvested SVF, freshly harvested PSC demonstrate potent in vivo tissue regeneration efficacy without pre-culture, which significantly streamlines the application of cell-based therapeutics for regenerative medicine. Other advantages of PSC use over SVF are similar to PSC advantages over cultured MSC and include precise characterization, and clearly defined product identity, purity, and potency.

The high BMP2 doses required for human osteogenesis are associated with life-threatening inflammatory cervical swelling [8], ectopic bone [37,38], osteoclastogenesis [39], and inconsistent bone formation [40,41]. Mechanistically, high dose BMP2 represses β-catenin-dependent Wnt signaling which inhibits osteogenesis [41] and promotes peroxisome proliferator activated receptor γ (PPARγ) expression and adipogenesis [42,43,44,45,46], leading to inefficient osteogenesis [40]. Wnt signals promote osteoblastic differentiation and activity, while inhibiting osteoclast function [47] and PPARγ expression and activity [42]. PPARγ is a key transcription factor promoting adipocyte differentiation [42]. Thus, many of the negative side effects of clinical BMP2 use can be predicted from BMP2's molecular mode of action.

In contrast, our published and unpublished data indicate that Nell-1 promotes Wnt and Runx2 signaling [48] while inhibiting PPARγ signaling. Runx2 is a key transcription factor promoting osteoblastic differentiation. From a safety and efficacy perspective, we find that transduced Nell-1 does not elicit inflammation, ectopic bone, osteoclastogenesis, or adipogenesis [49]. In fact, Nell-1 can negate BMP2 induced adipogenesis and promote more efficient bone formation [49,50]. Moreover, Nell-1, as a single agent, does not induce bone formation in muscle cells [50] or fibroblastic cells and mice over-expressing Nell-1 do not exhibit obvious ectopic bone growth and have a normal lifespan [Si], while non human primate (NHP) studies using rhNELL-1 did not document immunogenicity (anti-NELL-1 antibody formation), systemic/local toxicity or bioincompatibility. In addition, rhNELL-1 also does not induce inflammation, osteoclast activation, adipogenesis [49] or tumor growth [52].

From an efficacy perspective, studies described in the Examples demonstrate that Nell-1 reproducibly induces bone regeneration in various small animal models [50,53, 54,55] and more importantly, in large animal interbody spinal fusion models such as sheep [56] and non human primates (NHP). Importantly, in bone repair models not requiring ectopic bone formation, Nell-1 in an allograft carrier induces similar bone formation as BMP2 [53]. In sheep, direct comparison with BMP2 (InFUSE) shows that rhNELL-1 in an allograft bone carrier achieves comparable fusion without evidence of cyst formation (see the data in the Examples, below)). rhNELL-1 in an allograft carrier also induced fusion in non-human primates within 3 months—a time frame comparable to BMP2 (see the data in the Examples, below). Thus, from a molecular and clinical standpoint, use of Nell-1 may offer more specific and safer bone regeneration than BMP2.

Lastly, Nell-1 deficiency is neonatally lethal with major skeletal and vascular anomalies—indicating critical roles for Nell-1 not only during bone development, but vascular development as well [57,58,59]. With respect to vascular development, Nell-1 deficient mice exhibit significantly reduced Notch3 expression, which is important for promoting angiogenic activities of pericytes as well as smooth muscle cells and fibroblasts in vessel assembly, maturation and maintenance [59]. Thus, Nell-1 may normally induce angiogenic functions in endogenous pericyte.

Efficacy of human PSC+rhNELL-1 for Cell-Based Bone Regeneration

Successful cell-based bone regeneration requires: (1) sufficient osteogenic cell numbers; (2) scaffolds supporting osteogenic cell and vascular ingrowth; (3) factors to stimulate osteogenic differentiation, and ideally, vascular ingrowth. Our data indicate that rhNELL-1+PSC in an allograft carrier successfully meets these requirements.

With respect to pro-osteogenic NELL-1 effects on PSC in vitro, rhNELL-1 significantly increased human pericyte mineralization assessed by alizarin red staining (see the data in the Examples, below). rhNELL-1 also significantly increased Runx2 and Osx and decreased PPARγ expression prior to onset of mineralization (see the data in the Examples, below). In addition, ex vivo co-culture of PSC+ rhNELL-1 on an allograft carrier under osteogenic conditions markedly increased xylenol orange uptake (mineralization marker) (see the data in the Examples, below).

PSC are known to regulate endothelial cell proliferation, differentiation, survival, and capillary tube formation [60] and to potently stimulate angiogenesis and tissue ingrowth; in this regard we have observed that human pericytes injected into the infarcted mouse myocardium significantly augment local vascular density and reduce inflammatory monocyte/macrophage infiltration (data not shown). With respect to pro-angiogenic NELL-1 effects on PSC, rhNELL-1 significantly upregulates vascular endothelial growth factor (VEGF) expression in osteogenic differentiation medium maintained human PSC (see the data in the Examples, below). In addition, under non-osteogenic culture conditions, rhNELL-1 significantly increases proliferation of human PSC (see the data in the Examples, below). Meanwhile, implantation of human PSC+rhNELL-1+allograft carrier in SCID mouse thigh using lentiviral luciferase tagged PSC demonstrates significantly increased luciferase expression in rhNELL-1 treated animals vs. controls (see the data in the Examples, below). Collectively, these data indicate that Nell-1 specifically promotes human PSC survival, proliferation, angiogenic function, and osteoblastic differentiation.

With respect to in vivo bone formation and vascular ingrowth in a SCID mouse thigh implantation model, PSC+ rhNELL-1+allograft carrier showed significantly increased and more mature bone formation over rhNELL-1+allograft carrier, PSC+ allograft carrier, or allograft carrier alone at 3 weeks as well as marked bone sialoprotein (BSP) expression (see the data in the Examples, below). Meanwhile, all human PSC implantation groups demonstrate significantly increased endothelial von Willebrand Factor (vWF) staining in granulation tissue at one week (see the data in the Examples, below) and markedly upregulated VEGF expression at 2 weeks (see the data in the Examples, below). Remarkably, the VEGF staining intensity was significantly higher in the PSC+rhNELL-1+allograft carrier than the PSC+allograft carrier group (see the data in the Examples, below). Interestingly, staining with anti-MHC Class I antibody for human cells revealed increased VEGF production not only by implanted human PSC, but by murine host stromal cells as well (see the data in the Examples, below). Lastly, tagged PSC were still visible at 4 weeks on the surface of allograft bone in areas of active mineral deposition as well as along vessels (see the data in the Examples, below). These data demonstrate that implanted human PSC are angiogenic, trophic, (with said properties significantly enhanced by rhNELL-1), and when in the presence of rhNELL-1, osteogenic. These data establish the efficacy of human PSC+rhNELL-1 to promote bone formation and vascular ingrowth.

Compositions

In some embodiments, the composition of invention (sometimes also referred to as "PSC+NELL-1 composition") is capable of predictable local bone formation by delivering autologous adult perivascular stem cells (PSC) or iPS and an osteoinductive protein (NELL-1) on a bone scaffold. Such a scaffold can be synthetic scaffold or on an FDA-approved acellular allograft bone scaffold.

In one embodiment of the present invention, it is provided a method of bone regeneration using PSC or iPS and NELL-1 protein. Our solution—to prospectively purify perivascular ancestors of human mesenchymal stem cells (i.e., PSC) in stem cell rich adipose tissues and to use these non-cultured and pure stem cells of equivalent potential—may significantly overcome these drawbacks associated with the current tissue regeneration technologies using various stem cells. In addition, we have demonstrated that the combination of PSC with NELL-1 significantly increases PSC osteogenic and angiogenic efficiency.

The composition of invention creates a favorable environment for PSC or iPS differentiation toward bone regeneration; stem cells generally do not form bone without pre-culturing under osteogenic conditions [36,61] or treatment with osteoinductive factors [23]. The constituents of the PSC+NELL-1 composition provide a complete package of cells (PSC), osteoinductive factor (NELL-1), and scaffold (acellular allograft bone) to build an optimized microenvironment to "jump start" bone regeneration and vascular ingrowth.

Whether in the young or aged, the known consequences of delayed or unsuccessful bone regeneration are i) high medical costs, ii) lost productivity for patients and their caretakers and iii) adverse impact on quality of life and independent living. PSC or iPS has osteogenic, trophic, and angiogenic properties and can be combined with the osteoinductive NELL-1 protein to create a PSC+NELL-1 product that exceeds the efficacy and safety of current bone regeneration therapies.

Advantages of the present invention can include, but are not limited to, (1) when combined with NELL-1, adipose derived PSC can be a safer and more efficacious stem cell source to use for bone regeneration (i.e., PSC can more effectively form bone than the total stromal vascular fraction (SVF), while PSC can form bone just as effectively as ASC (but minus the need for ex vivo culture—and hence, safer), and (2) composition comprising PSC and NELL-1 can form bone more effectively with fewer adverse effects than autograft bone or BMP2 based bone graft products (e.g., INFUSE® Bone Graft).

The composition disclosed herein can be applied to or used in any site where bone regeneration is desired. In some embodiments, the composition can be used in spine fusion, and the composition can be implanted wherever autologous bone graft is indicated. Spine fusion is practiced to treat different disorders of the spine including degenerative conditions, deformities, trauma based disorders, and spinal tumors [62]. The increasing cases of spine related diseases coupled with the growing aged population (as older people are more prone to spine-related diseases) can significantly increase the need for spine fusion surgery [62].

Other important advantages of the composition of the present invention include, e.g., autologous, non-cultured PSC use may avoid the safety risks of immunogenicity, infection, and potential genetic instability/tumorigenicity [17,18] associated with conventional BMSC or ASC use. Non-purified human stromal vascular fraction PSC have been infused into humans without adverse effects [63]. Mice over-expressing Nell-1 do not exhibit obvious ectopic bone growth and have a normal lifespan [Si], while administration of NELL-1 to non-human primates did not elicit immunogenicity (anti-NELL-1 antibody formation), systemic/local toxicity or bioincompatibility. In addition, NELL-1 does not induce inflammation, osteoclast activation, bone cyst formation [10,11] or tumor growth [64]. PSC+NELL-1 is contraindicated in pregnancy, active operative site infection, active malignancy, and skeletal immaturity.

As demonstrated by Examples described below, the composition of invention shows specific bone generation properties. For example, increased mineralization of PSC+NELL-1, relative to PSC alone demonstrates in vitro product activity. Promotion of equivalent or superior/faster bone formation and spine fusion by PSC+NELL-1 relative to autologous bone grafts or BMP2 in animal models demonstrates in vivo product activity. The composition is safe and absent immune response (antibodies to NELL-1), as well as 1—higher fusion rate and maintenance of disc height (X-rays and CT scans), and 2—less pain, improved function and neurological status relative to autograft bone or BMP2.

As used herein, the term fusion for animal and human studies is defined as the presence of bridging bone connecting the inferior and superior vertebral bodies that is over 50% of the implant volume.

The composition of the present invention can appear in any desired formulation for bone regeneration. For example, the composition can be an implant to be implanted in lieu of an autologous bone graft or BMP2 (INFUSE®) during spine fusion surgery. The composition can be formulated using established methodology to meet desirable release criteria for each of PSC or iPS and NELL-1 for a given formulation. For example, as a spine fusion implant, the composition can meet release criteria for each of the PSC or iPS and NELL-1 constituents.

Compositions of present invention are advantageous over existing osteogenic technologies: first, the immediate use of autologous PSC is preferred over embryonic stem cells (ESC) or mesenchymal stem cells (MSC) since the risk of teratoma formation and need for immunosuppression with ESC and the requirement for animal products and prolonged culture [17] with ESC and MSC remain significant safety issues [24,25]. Second, relative to the lower cell yield (~104 stem cells/40 ml) and limited donor sites for bone marrow aspirates, adipose tissue is a well documented, easily accessible, abundant (~106 stem cells/40 ml), and dispensable source of such cells [15,26,27]. Third, although the use of the non-cultured total stromal vascular fraction (SVF) from adipose tissues may remove the need for ex vivo culture, available studies using SVF show lower bone regeneration efficacy relative to cultured adipose derived stem cells (ASC) [31,32,33]. In this regard, there is increasing evidence that endothelial cells present in SVF negatively regulate the differentiation potential of MSC such as ASC or BMSC [19,20]. For instance, human endothelial cells inhibit BMSC differentiation into mature osteoblasts by interfering with Osterix expression, a gene critical for osteoblastic differentiation [20]. Endothelial cells also inhibit the adipogenic differentiation of ASC [19]. Lastly, in the current absence of characterized osteogenesis restricted progenitor cells, multipotent MSC which can be derived from multiple adult organs, including adipose tissue, are commonly envisioned to regenerate bone [7,22]. However, MSC have been only retrospectively isolated in long-term culture. In addition to the aforementioned risks attached to the presence of animal products in culture media [17] and genetic instability consecutive to sustained ex vivo proliferation [18], MSC are a heterogeneous cell population of which composition and native embryonic derivation, identity and frequency have been unknown. The osteogenic properties of MSC being well established[7,22], these drawbacks could be circumvented if native MSC could be prospectively extracted from human tissues. This possibility has been opened by the recent identification, largely by our own group, of ubiquitous perivascular ancestors of MSC.

Perivascular Stem Cells

As used herein, the term perivascular stem cells (PSC) shall encompass pericyte and adventitia cells.

Isolation of PSC are well documented. For example, pericyte cells were isolated from various tissues by Peault and Huard in U.S. application Ser. No. 11/746,979. Isolation of adventitial cells from various tissues are well documented (data not shown).

PSC have been isolated from essentially all tissues tested including skeletal muscle, pancreas, placenta, adipose, brain, heart, skin, lung, eye, gut, bone marrow, umbilical cord, or teeth. In some embodiments, autologous PSC are purified through fluorescence activated cell sorting (FACS) [36] from the stromal vascular fraction of adipose tissues in numbers sufficient to achieve clinical efficacy without ex vivo expansion. The following describes an example of isolating PSC from human skeletal muscle tissues:

Isolation of PSC.

Briefly, skeletal muscle is separated from fat and macro vasculature then minced into small pieces. The muscle is then incubated (e.g., for 45 min at 37° C.) in medium containing DMEM high glucose (Gibco), 20% FBS (Gibco), 1% Penicillin-Streptomycin (PS) (Gibco) and complemented by 0.5 mg/ml of each collagenases type I, II, and IV. The resulting cell suspension was filtered to eliminate all debris. After rinsing, cells are FACS-sorted according to positive expression for CD 146, NG2 (a proteoglycan associated with pericytes during vascular morphogenesis) and PDGF-Rβ, and to the absence of hematopoietic (CD45), endothelial (CD34), and myogenic (CD56) cell markers. The dead cells are excluded by FACS via propidium iodure staining. Sorted pericytes are seeded (e.g., at $2 \times 10^4$ cells/$cm^2$ in endothelial cell growth medium 2 (EGM-2, Cambrex Bioscience)) and cultured (e.g., at 37° C. for 2 weeks in plates coated with 0.2% gelatin (Calbiochem)). Pericytes are trypsinized once a week and cultured (e.g., at 1:3 dilution (from passage 1 to 5) then at 1:10 (after passage 5)). Except for the first passage, all pericytes are cultured (e.g., in DMEM/FBS/PS proliferation medium) in uncoated flasks to maintain their original phenotype. Pericytes between passages 9 and 11 are used for all tests.

Isolation of adventitia PSC is exemplified by the procedure described in Example 2.

NELL-1 Factor

"A NELL-1 factor" as used herein, includes wild type (i.e., naturally occurring) Nell 1 proteins of any mammalian origin, such as human, murine, rat and the like. Exemplary NELL-1 factors for use in the present invention include human NELL-1 protein (SEQ ID NO: 1), murine NELL-1 protein (SEQ ID NO: 2), and rat NELL-1 protein (SEQ ID NO: 3).

"A NELL-1 factor" as used herein, also includes functional derivatives of a wild type NELL-1 protein. A "functional derivative" refers to a modified NELL-1 protein which has one or more amino acid substitutions, deletions or insertions as compared to a wild type NELL-1 protein, and which retains substantially the activity of a wild type NELL-1 protein. By "substantially" is meant at least 50%, at least 75%, or even at least 85% of the activity of a wild type NELL-1 protein. According to the present invention, in order for the functional derivative to substantially retain the activity or function of a wild type NELL-1 protein, the functional NELL-1 derivative shares a sequence identity with the wild type NELL-1 protein of at least 75%, at least 85%, at least 95% or even 99%.

The structure of NELL-1 proteins has been characterized (see, e.g., Kuroda et al., 1999a; Kuroda et al., 1999b, Desai et al., 2006). For example, the murine NELL-1 protein (SEQ ID NO: 4) is a protein of 810 amino acids, having a secretion signal peptide (amino acids #1 to 16), an N-terminal TSP-like module (amino acids #29 to 213), a Laminin G region (amino acids #86 to 210), von Willebrand factor C domains (amino acids #273 to 331 and 699 to 749), and a $Ca^{2+}$-binding EGF-like domains (amino acids #549 to 586).

The secretion signal peptide domain of NELL-1 protein is an amino acid sequence in the protein that is generally involved in transport of the protein to cell organelles where it is processed for secretion outside the cell. The N-terminal TSP-like module is generally associated with heparin binding. von Willebrand factor C domains are generally involved with oligomerization of NELL-1. Laminin G domains of NELL-1 protein are generally involved in adherence of NELL-1 protein to specific cell types or other extracellular matrix proteins. The interaction of such domains with their counterparts is generally associated with, for example, processes such as differentiation, adhesion, cell signaling or mediating specific cell-cell interactions in order to promote cell proliferation and differentiation. The $Ca^{2+}$-binding EGF-like domains of NELL-1 binds protein kinase C beta, which is typically involved in cell signaling pathways in growth and differentiation.

The amino acid sequence of NELL-1 protein is very highly conserved, especially across mammalian species. For example, the murine NELL-1 protein shares about 93% sequence identity with the human NELL-1 protein (SEQ ID NO: 1), which, in turn, shares about 90% sequence identity with the rat NELL-1 protein (SEQ ID NO: 2). Those skilled in the art can use any of the well-known molecular cloning techniques to generate NELL-1 derivatives having one or more amino acid substitutions, deletions or insertions, taking into consideration the functional domains (e.g., secretion signal peptide sequence, N-terminal TSP-like module, Laminin G region, von Willebrand factor C domain) of NELL-1. See, for example, Current Protocols in Molecular Cloning (Ausubel et al., John Wiley & Sons, New York).

The minimum length of a NELL-1 functional derivative is typically at least about 10 amino acids residues in length, more typically at least about 20 amino acid residues in length, even more typically at least about 30 amino acid residues in length, and still more typically at least about 40 amino acid residues in length. As stated above, wild type NELL-1 protein is approximately about 810 amino acid residues in length. A NELL-1 functional derivative can be at most about 810 amino acid residues in length. For example, a NELL-1 functional derivative can be at most at most about 820, 805, 800, 790, 780, 750, 600, 650 600, 550, etc. amino acid residues in length.

Once a NELL-1 protein derivative is made, such protein can be tested to determine whether such derivative retains substantially the activity or function of a wild type NELL-1 protein. For example, the ability of a NELL-1 derivative to bind PKC beta can be tested. Suitable assays for assessing the binding of NELL-1 to PKC beta is described in e.g., Kuroda et al. (1999b). For example, protein-protein interaction can be analyzed by using the yeast two-hybrid system. Briefly, a modified NELL-1 protein can be fused with GAL4 activating domain and the regulatory domain of PKC can be fused with the GAL4 DNA-binding domain. The activity of beta-galactosidase in yeast cells can be detected.

In addition, one can also test the ability of a NELL-1 derivative to stimulate differentiation of precursor cells, which are in the osteoblast lineage, towards mature osteocytes. Maturity of osteocytes can be assessed cellularly (histology) and molecularly (expression of cardiac-specific proteins or extracellular matrix materials). Still further, a NELL-1 derivative can be tested for its ability to drive osteoblast precursors to mature bone cells, by detecting expression of late molecular bone markers or mineralization (i.e., calcium deposits). By comparing the activity of a NELL-1 derivative with that of a wild type NELL-1 protein in one or more of the assays such as those described above, one should be able to determine whether such derivative retains substantially the activity or function of a wild type NELL-1 protein.

A NELL-1 protein or functional derivative thereof may be prepared by methods that are well known in the art. One such method includes isolating or synthesizing DNA encoding the NELL-1 protein, and producing the recombinant protein by expressing the DNA, optionally in a recombinant vector, in a suitable host cell, including bacterial, yeast, insect or mammalian cells. Such suitable methods for synthesizing DNA are, for example, described by Caruthers et al. 1985. Science 230:281-285 and DNA Structure, Part A: Synthesis and Physical Analysis of DNA, Lilley, D. M. J. and Dahlberg, J. E. (Eds.), Methods Enzymol., 211, Academic Press, Inc., New York (1992).

As used herein, the term "therapeutically effective amount" means the dose of NELL-1 factor required for causing a PSC or iPS to differentiate into a bone tissue cell or progenitor cell to achieve bone tissue regeneration or for enhancing the survivability or engraftment of the PSC or iPS where PSC or iPS provide trophic factors or enhance vascular ingrowth so as to treat, delay, or ameliorate a bone condition, which is further described below.

NELL-1 protein and method of making the protein has been described in U.S. application Ser. Nos. 10/544,553, 11/392,294, 11/713,366, and 11/594,510, and U.S. Pat. No. 7,052,856. The teachings in these applications and patent are incorporated herein by reference.

NELL-1 protein and method of making the protein have been described in U.S. application Ser. Nos. 10/544,553, 11/392,294, 11/713,366, and 11/594,510, and U.S. Pat. No. 7,052,856. The teachings in these applications and patent are incorporated herein by reference.

Formulations and Carriers

The composition disclosed herein can be formulated into any formulation of choice. The composition can include materials and carriers to effect a desired formulation. For example, the composition can include an injectable or moldable material that can set within a pre-defined period of placement. Such a pre-defined period can be, e.g., 10 minutes, 30 minutes, one hour, two hours, etc.

In some embodiments, the composition can include a chemical gel that includes primary bonds formed due to changes in pH, ionic environment, and solvent concentration. Examples of such chemical gels can be, but are not limited to, polysaccharides such as chitosan, chitosan plus ionic salts such as beta-glycerophosphates, alginates plus $Ba^{2+}$, $Sr^{2+}$, $Ca^{2+}$, $Mg^{2+}$, collagen, fibrin, plasma or combinations thereof.

In some embodiments, the composition can include a physical gel that includes secondary bonds formed due to temperature changes. Examples of such physical gels can be, but are not limited to, alginate, poly(ethylene glycol)-poly (lactic acid-co-glycolic acid)-poly(ethylene glycol) (PEG-PLGA-PEG) tri-block copolymers, agarose, and celluloses. In some embodiments, physical gels that can be used in the composition described herein can include physical gels that are liquid under high shear but gels to solid at low shear. Examples of such physical gels include, but are not limited to, hyaluronic acid, or polyethylene oxides. The physical gels can have pre-formed materials with pre-defined dimensions and shape.

In some embodiments, the composition described herein can include a material that degrades or releases active agents in response to a stimulus. Some examples of such stimuli are mechanical stimuli, light, temperature changes, pH changes, change of ionic strength, or electromagnetic field. Such materials are known in the art. Some examples of such materials are chitosan, alginates, pluronics, methyl cellulose, hyaluronic acids, and polyethylene oxides. Other examples are described by Brandl F, Sommer F, Goepferich A. "Rational design of hydrogels for tissue engineering: Impact of physical factors on cell behavior" in Biomaterials. Epub 2006 Sep. 29.

In some embodiments, the composition described herein can include a gel containing any of hydroxyapatites, apatites, tricalcium phostphates, calcium phosphates, bioactive glass, demineralized bone matrix, human allograft bone and cartilage, human autograft bone, bovine bone and cartilage, other materials commonly included in allograft bone, or mixtures thereof.

In some embodiments, the composition described herein including any of the gels described above can further include a crosslinker to further tailor degradation kinetics and controlled release. Alternatively, in some embodiments, the composition described herein can include an interpenetrating phase composite or interpenetrating network (IPN) that includes any of the above described gels. Some examples of the crosslinker include, but are not limited to, common crosslinking agents (polyalkylene oxide, ethylene dimethacrylate, N,N'-methylenebisacrylamide, methylenebis(4-phenyl isocyanate), ethylene dimethacrylate, divinylbenzene, allyl methacrylate, carbodiimidazole, sulfonyl chloride, chlorocarbonates, n-hydroxysuccinimide ester, succinimidyl ester, epoxides, aryl halides, sulfasuccinimidyl esters, and maleimides); PEG based crosslinkers (e.g. MAL-dPEGx-NHS-esters, MAL-dPEGx acid, Bis-MAL-dPEGx, etc.) and photo/light activated crosslinkers, N-hydroxysuccinimide-based crosslinkers, dilysine, trilysine, and tetralysine.

The composition described herein can include a carrier. The carrier can be a polymeric carrier or non-polymeric carrier. In some embodiments, the carrier can be biodegradable, such as degradable by enzymatic or hydrolytic mechanisms. Examples of carriers include, but are not limited to synthetic absorbable polymers such as such as but not limited to poly($\alpha$-hydroxy acids) such as poly (L-lactide) (PLLA), poly (D, L-lactide) (PDLLA), polyglycolide (PGA), poly (lactide-co-glycolide (PLGA), poly (-caprolactone), poly (trimethylene carbonate), poly (p-dioxanone), poly (-caprolactone-co-glycolide), poly (glycolide-co-trimethylene carbonate) poly (D, L-lactide-co-trimethylene carbonate), polyarylates, polyhydroxybutyrate (PHB), polyanhydrides, poly (anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly (glaxanone), polysaccharides, and poly(orthoesters), polyglactin, polyglactic acid, polyaldonic acid, polyacrylic acids, polyalkanoates; copolymers and admixtures thereof, and any derivatives and modifications. See for example, U.S. Pat. No. 4,563,489, and PCT Int. Appl. No. WO/03024316, herein incorporated by reference. Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

In one embodiment, the carrier can further be coated by compositions, including bioglass and or apatites derived from sol-gel techniques, or from immersion techniques such as, but not limited to simulated body fluids with calcium and phosphate concentrations ranging from about 1.5 to 7-fold the natural serum concentration and adjusted by various means to solutions with pH range of about 2.8-7.8 at temperature from about 15-65 degrees C. See, for example, U.S. Pat. Nos. 6,426,114 and 6,013,591; and PCT Int. Appl. WO/9117965 herein incorporated by reference.

Other examples of carriers include collagen (e.g. Collastat, Helistat collagen sponges), hyaluronan, fibrin, chitosan, alginate, and gelatin. See for example, PCT Int. Appls. WO/9505846; WO/02085422, herein incorporated by reference.

In one embodiment, the carrier can include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity. See for example, Journal of Biological Chemistry (2003), 278(44), p. 43229-43235, herein incorporated by reference.

In one embodiment, the composition can be in the form of a liquid, solid or gel. In one embodiment, the substrate can include a carrier that is in the form of a flowable gel. The gel can be selected so as to be injectable, such as via a syringe at the site where cartilage formation is desired. The gel can be a chemical gel formed by primary bonds, and controlled by pH, ionic groups, and/or solvent concentration. The gel can also be a physical gel which can be formed by secondary bonds and controlled by temperature and viscosity. Examples of gels include, but are not limited to, pluronics, gelatin, hyaluronan, collagen, polylactide-polyethylene glycol solutions and conjugates, chitosan, chitosan & $\beta$-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263(4), 342-349, herein incorporated by reference.

In one embodiment, the carrier can be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate. See for example, U.S. Pat. No. 5,410,016, herein incorporated by reference.

In one embodiment, the composition can include a carrier that is temperature sensitive. Examples include carriers made from N-isopropylacrylamide (NiPAM), or modified NiPAM with lower critical solution temperature (LCST) and enhanced peptide (e.g. NELL-1) binding by incorporation of ethyl methacrylate and N-acryloxysuccinimide; or alkyl methacrylates such as butylmethacrylate, hexylmethacrylate and dodecylmethacrylate. PCT Int. Appl. WO/2001070288; U.S. Pat. No. 5,124,151 herein incorporated by reference.

In one embodiment, where the carrier can have a surface that is decorated and/or immobilized with cell adhesion molecules, adhesion peptides, and adhesion peptide analogs which can promote cell-matrix attachment via receptor mediated mechanisms, and/or molecular moieties which can promote adhesion via non-receptor mediated mechanisms binding such as, but not limited to polycationic polyamino-acid-peptides (e.g. poly-lysine), polyanionic polyamino-acid-peptides, Mefp-class adhesive molecules and other DOPA-rich peptides (e.g. poly-lysine-DOPA), polysaccharides, and proteoglycans. See for example, PCT Int. Appl. WO/2004005421; WO/2003008376; WO/9734016, herein incorporated by reference.

In one embodiment, the carrier can include various naturally occurring matrices or their components such as devitalized cartilage matrix, demineralized bone matrix, or other components derived from allograft, xenograft, or any other naturally occurring material derived from Monera, Protista, Fungi, Plantae, or Animalia kingdoms.

In one embodiment, the carrier can include one or more sequestering agents such as, but not limited to, collagen, gelatin, hyaluronic acid, alginate, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, blood, fibrin, polyoxyethylene oxide, calcium sulfate hemihydrate, apatites, carboxyvinyl polymer, and poly(vinyl alcohol). See for example, U.S. Pat. No. 6,620,406, herein incorporated by reference.

In one embodiment, the carrier can include surfactants to promote stability and/or distribution of the NELL-1 peptide within the carrier materials such as, but not limited to polyoxyester (e.g. polysorbate 80, polysorbate 20 or Pluronic F-68).

In one embodiment, the carrier can include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier can include a combination of materials such as those listed above. By way of example, the carrier can a be a PLGA/collagen carrier membrane. The membrane can be soaked in a solution including NELL-1 peptide.

An implant can include a substrate formed into the shape of a stent, mesh, pin, screw, plate, or prosthetic joint. An implant can include a substrate that is resorbable, such as a substrate including collagen.

The composition can also include an acceptable carrier to form a pharmacological composition. Acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a carrier, including a physiologically acceptable compound depends, for example, on the route of administration.

The compositions can be administered in a variety of unit dosage forms depending upon the method of administration. For example, unit dosage forms suitable can include powder, or injectable or moldable pastes or suspension.

The compositions of this invention can comprise a pharmaceutically acceptable carrier, such as an aqueous carrier for water-soluble peptides. A variety of carriers can be used, e.g., buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of NELL-1 peptide in these formulations can vary widely, and are selected primarily based on fluid volumes, viscosities, body weight and the like in accordance with the particular mode of administration selected and the patient's needs.

The composition can include the PSC or iPS in various density of population, for example, a density from about $1\times10^4$ to about $1\times10^8$/mL (per 1 mL volume of the composition). In some embodiments, the seeding density can be from about $1\times10^4$ to about $1\times10^6$, from about $1\times10^4$ to about $1\times10^5$, from about $1\times10^5$ to about $1\times10^7$, from about $1\times10^5$ to about $1\times10^6$, from about $1\times10^6$ to about $1\times10^7$/ml, or from about $1\times10^7$ to about $1\times10^8$/ml. Examples of seeding densities can be, e.g., $0.5\times10^4$, $1\times10^4$, $0.5\times10^5$, $1\times10^5$, $0.5\times10^6$, $1\times10^6$, $0.5\times10^7$, $1\times10^7$, or $1\times10^8$/ml.

The dosage regimen for NELL-1 is determined by the clinical indication being addressed, as well as by various patient variables (e.g. weight, age, sex) and clinical presentation (e.g. extent of injury, site of injury, etc.). Generally, the NELL-1 is in a concentration sufficient to cause a PSC or iPS to differentiate into an osteogenic cell or progenitor cell. Such osteogenic cells include, e.g., osteoblasts, at various steps of the hierarchy of osteogenesis.

Dosages of NELL-1 can be determined according to methods known in the art based on type of agent, the disease, and other factors such as age and gender.

In one embodiment, the dosage of NELL-1 factor can be described in terms of an amount per unit area of a composition or per unit weight of a composition. The dosage of NELL-1 generally ranges from 0.001 pg/mm² to 1 pg/mm², or more preferably from 0.001 ng/mm² to 1 ng/mm², or more preferably from 0.001 µg/mm² to 1 µg/mm², or more preferably from 0.001 mg/mm² to 1 mg/mm², or more preferably from 0.001 g/mm² to 1 g/mm², with or without a particular carrier or scaffold. In another embodiment, the dosage of NELL-1 generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage of NELL-1 generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold.

In some embodiments, the NELL-1 dosage can be described in terms of an amount per kilogram of body weight. For example, for the administration to adult humans, the dosage of NELL-1 can range from about 0.1 µg to about 100 mg per kilogram of body weight. In some embodiments, a suitable dose of a NELL-1 composition for the administration to adult humans is in the range of about 0.001 mg to about 20 mg per kilogram of body weight. In some embodiments, a suitable dose of a NELL-1 composition for the administration to adult humans is in the range of about 0.005 mg to about 10 mg per kilogram of body weight. In some embodiments, a suitable dose of a NELL-1 composition for the administration to adult humans is in the range of about 0.01 mg to about 5 mg per kilogram of body weight. In some embodiments, a suitable dose of a NELL-1 composition for the administration to adult humans is in the range of about 0.05 mg to about 1.0 mg per kilogram of body weight. However, the precise dosage to be therapeutically effective and non-detrimental can be determined by those skilled in the art.

Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

Method of Fabrication

Generally, the method of making the composition comprises the acts of
a) providing an osteoinductive agent (e.g, a NELL-1 factor),
b) providing a population of PSC or iPS, and
c) forming the composition,
wherein the osteoinductive agent is in a therapeutically effective amount for causing the PSC or iPS to differentiate in the osteoblast lineage or in a therapeutically effective amount for enhancing the survivability or engraftment of the PSC or iPS where PSC or iPS provide trophic factors or enhance vascular ingrowth so as to treat, delay, or ameliorate a bone condition.

In some embodiments, forming comprises forming a formulation comprising the NELL-1 protein, and seeding the formulation with a population of the PSC or iPS. In some embodiments, the formulation can further comprise an excipient, e.g., which is further described below.

The formulation can take any dosage form. In some embodiments, its is a powder formulation. In some embodiments, it is a liquid formulation. In some embodiments, it is a semi-solid/semi-liquid formulation, e.g., a gel or paste. In some embodiments, the formulation is an implantable device such as a bone implant. In some embodiments, the formulation is a scaffold.

The formulation can take any desirable form for seeding a population of PSC or iPS. In some embodiments, where the formulation is a scaffold or an implant, the formulation can be porous for seeding the PSC or iPS. The pores in the formulation can have a volume that is capable of accommodating the seeding density of the PSC or iPS.

Seeding of the PSC or IPS can be achieved by well established cell seeding procedures (see, e.g., Undale, et al., Mayo Clin Proc., 84(1):893-902 (2009); Cancedda et al., Biomaterials 28: 4240-4250 (2007); and Marcacci, et al., Tissue Engineering, 13(5):947-955 (2007)) and can vary according to the dosage form of the composition. For example, for liquid formulations, seeding can be readily achieved by placing a population in the formulation. An example of seeding a porous implant or scaffold is described in Wei He, et al., Pericyte-Based Human Tissue Engineered Vascular Grafts, in Biomaterials (in press).

The seeding density for PSC or iPS can vary from about $1 \times 10^4$ to about $1 \times 10^8$/mL (per 1 mL volume of the composition). In some embodiments, the seeding density can be from about $1 \times 10^4$ to about $1 \times 10^6$, from about $1 \times 10^4$ to about $1 \times 10^5$, from about $1 \times 10^5$ to about $1 \times 10^7$, from about $1 \times 10^5$ to about $1 \times 10^6$, from about $1 \times 10^6$ to about $1 \times 10^7$/ml, or from about $1 \times 10^7$ to about $1 \times 10^8$/ml. Examples of seeding densities can be, e.g., $0.5 \times 10^4$, $1 \times 10^4$, $0.5 \times 10^5$, $1 \times 10^5$, $0.5 \times 10^6$, $1 \times 10^6$, $0.5 \times 10'$, $1 \times 10^7$, or $1 \times 10^8$/ml.

The following describes an example of seeding the PSC or iPS in a scaffold:

Seeding of PSC.

A PSC suspension is seeded into the ES-TIPS PEUU scaffolds via a vacuum rotational seeding device described by Soletti et al., Biomaterials, 27(28):4863-70 (2006). In brief, a scaffold is connected to two coaxial stainless steel tees inside an airtight chamber. The chamber is connected to house vacuum to maintain a negative and constant pressure (−130 mmHg), which induces transmural flow of the cell suspension across the scaffold. A syringe pump infuses the cell suspension ($1 \times 10^6$ cells/mL) at 2.5 mL/min into the manually rotating scaffold to reach $3 \times 10^6$ cells per scaffold within less than 2 min, resulting in a scaffold with uniformly distributed cells. Seeded scaffolds are immediately put into static culture for 3 hours, which is sufficient for cellular attachment (see, e.g., Soletti, et al., Biomaterials, 29(7):825-33 (2008)). Scaffolds are then transferred to a spinner flask with 200 mL medium at 15 rpm stirring for 2 days of culture, after which it is implanted into the rat.

Scaffolds are observed under SEM immediately after seeding. The seeded scaffolds after 2 days' dynamic culture are further assessed for histology (H&E), cellular distribution (F-actin and nuclear staining), and attachment (SEM). For F-actin staining, cryosections are permeabilized (0.1% Triton) for 30 min, blocked (2% BSA) for 30 min and then incubated with Alexa 488-conjugated phalloidin (1:500, Sigma) for 1 hour.

Method of Use

The composition described herein can be administered to a mammal (e.g., a human being) for treating, preventing or ameliorating a bone or vertebra related condition in the mammal. In some embodiments, the bone related conditions includes fractures such as femoral neck fracture, neck bone fracture and wrist fracture, cancer and injury-induced defect, disease-related bone loss, such as bone loss after tooth extraction and periodontal disease-related bone loss, weakened bone quality, arthritis, osteolysis and other degenerative changes or healing of bone tissues, such as in jaw bone, refractory bone wound healing, delayed bone healing, bone healing accompanied with bone resorption or conditions that require the placement of metallic and non-metallic implants to stabilize or fix and reconstruction of bone tissues such as total hip replacement. In some embodiments, the bone condition described herein can be conditions in the jaw and craniofacial areas. The method includes administering the composition to a patient having any of such conditions.

The vertebral related conditions includes spine fracture/disorder or spinal disk displacement, fracture or degenerative changes of vertebral tissues, bone and other tissue defect, recession and degenerative changes caused by cancer, injury, systemic metabolism, infection or aging, or fixation and reconstructive treatment of vertebral tissues.

The mode of administration can be implanting, direct injection, coating on metallic or non-metallic artificial implants, or placing around an implant (e.g., a metallic or non-metallic artificial implant). Some examples of delivering the composition can be, e.g., percutaneous injection through intact skin to various sites, or direct injection through nonintact skin (e.g., surgically opened sites or trauma sites). In some embodiments, the delivery can be surgical implantation of a composition described herein. In some embodiments, the delivery can be one of extravascular delivery, injection or catheter based injections; intravascular delivery, injection or catheter based injections; intravenous delivery, injection or catheter based injections; intraarterial delivery, injection or catheter based injections; intrathecal delivery, injection or catheter based injections; intraosseous delivery, injection or catheter based injections; intracartilaginous delivery, injection or catheter based injections; or intravesical delivery, injection or catheter based injections.

In some embodiments, a delivery of composition described herein to a mammalian subject can be delivery via mechanical pumps with percutaneous or implantable catheters.

In some embodiments, a delivery of composition described herein to a mammalian subject can be catheter based delivery to any area/organ in the body.

In some embodiments, a delivery of composition described herein to a mammalian subject can be delivery via expanded dispersion through various devices promoting increased tissue penetration or wider tissue distribution (e.g., ultrasound, iontophoresis, heat, pressure, etc.)

EXAMPLES

The embodiments of the present invention are illustrated by the following set forth examples. All parameters and data do not limit the scope of the embodiments of the invention.

Example 1. Studies on PSC+NELL-1 Composition for Osteogenesis

General Methods

In vitro efficacy is evaluated by trophic factor production and osteogenic differentiation; in vitro safety by genetic stability; in vivo efficacy and safety by imaging, surgical pathology, histology, immunohistochemistry, and cell tracking studies.

Note, as used in the examples, the terms "optimized" or "opt" are used to designate an embodiment or embodiments that achieves a better result or results under given conditions. These terms shall in no way be construed as the preferred embodiments or best modes of the present invention.

Discussions

In the studies described herein, we have developed an adult, perivascular stem cell based PSC+NELL-1 combination product that exceeds the efficacy and safety of current bone regeneration therapies. The studies show that when combined with NELL-1, adipose derived PSC are a safer and more efficacious stem cell to use for bone regeneration.

We have marked and purified to homogeneity two distinct human perivascular cell populations: microvascular pericytes (CD146+CD34−CD45−CD31−) and adventitial cells (CD146−CD34+CD45−CD31−). These cells, just isolated or cultured over the long term, are indistinguishable from conventional MSC—hence the collective term perivascular stem cells or PSC [36]. PSC are robustly osteogenic in culture and in vivo, migrate actively, stimulate angiogenesis and secrete diverse growth factors [36,65]. We have demonstrated that PSC can be purified in sufficient numbers from fat tissue without the need for culture expansion (Data not shown). Importantly, we have determined that our PSC purification protocol enables the isolation of all multipotent stem cell populations, free of endothelial cells, from all human tissues tested thus far. In summary, advantages of PSC over MSC include: 1—no need for culture (may decrease risks of immunogenicity, infection, and genetic instability [17,18]), 2—precise characterization in terms of native tissue localization, phenotype and developmental potential (conversely, MSC are only retrospectively derived from primary, heterogeneous cell cultures), and 3—improved trophic potency [we have determined that PSC secrete 10-20 times more heparin binding epidermal growth factor (HB-EGF) and 3-7 times more basic fibroblast growth factor (FGF) and vascular endothelial growth factor (VEGF) than classically derived adipose tissue and cord blood MSC [29]]. Thus from an FDA regulation perspective, using PSC can facilitate demonstration of consistency in product identity, purity, and potency.

NELL-1 is used to provide PSC or iPS within an osteoinductive environment to promote predictable bone growth. NELL-1 reproducibly induces bone regeneration in various small animals [50,53,54,55] and in interbody spinal fusion models in sheep [56] and non-human primates. The high osteospecificity of NELL-1 derives in part from its direct regulation by Runx2, the master control gene for osteoblast differentiation [66]. NELL-1 specifically suppresses adipogenesis and peroxisome proliferator activated receptor γ (PPARγ) signaling, while promoting β-catenin-dependent Wnt signaling, in bone marrow MSC [49], making this growth factor suitable for aged or osteoporotic individuals where adipogenic differentiation of bone marrow stem cells contributes to the pathogenesis of bone loss [6,67]. The studies below show the potent effect, in culture and in vivo, of NELL-1 on purified PSC in terms of osteogenesis promotion.

Osteoinduction Studies

1. Comparison Studies on hPSC Safety/Efficacy with that of hSVF Cells

The studies show that when combined with NELL-1, adipose derived PSC are a safer and more efficacious stem cell source to use for bone regeneration. The studies demonstrate that human PSC are at least as efficient, and possibly superior to total tissue stroma (the adipose tissue SVF in this case) and conventional, in vitro derived MSC in terms of cell viability, purity, stem cell content, trophic factor production, osteogenic differentiation, maintaining genetic stability (tumorigenicity), fate/survival, angiogenesis and osteogenesis.

Methods and Techniques

1—adipose tissue derived PSC (i.e., pericytes and adventitial cells sorted by FACS, mixed but not expanded in vitro) are compared with 2—the non-cultured total stromal vascular fraction (SVF, i.e., total fat, less the adipocytes), 3—the same PSC population as in 1, maintained in culture, and 4—ASC (adipose tissue derived stem cells) derived conventionally from primary long term culture of the SVF, all from the same human lipoaspirate sample. All cultured cells are tested after 1, 4, 8 and 14 passages. To ensure reproducibility, similar studies are performed with several lipoaspirate samples from different donors controlled for age (young vs. old), sex, sample anatomic location, and body mass index. Our tests showed NELL-1 positively affected PSC survival/proliferation and differentiation (data not shown), which is further supported by the examples in FIGS. 10 and 11.

Lipoaspirates, SVF and PSC are isolated per protocol [68]. Relative percentages of pericytes (CD146+NG2+PDGF-Rβ+CD34−CD31−CD45−) and adventitial cells (CD146−NG2−PDGF-Rβ−CD34+CD31−CD45−) are quantified in the SVF, and in the cultured ASC and PSC cell populations. Endothelial cell (CD34+CD31+CD45−) numbers are also measured in the SVF and ASC cell fractions, as these cells may inhibit the differentiation of PSC. Initial viability of PSC and SVF fractions recovered from lipoaspirate are determined with DAPI staining and flow cytometry analysis. Cell purity is assessed by comparing FACS results from PSC—pre-cultured or not—, SVF and ASC as well as real time PCR(RT-PCR) analysis of endothelial, hematopoietic, and fibroblast lineage markers. As an approximation of mesenchymal stem cell content, SVF and PSC are seeded at low density to test and quantify their ability to give rise to clonal fibroblast (CFU-F) and osteoblastic (CFU-OB) colonies. To evaluate the maintenance of MSC progenitors over time, CFU-F and CFU-OB assays are performed on cultured PSC and cultured SVF-derived ASC as described [69]. Production of trophic factors (HB-EGF, VEGF, FGF, and PDGF-BB) by cultured cells is measured using a multiplexed sandwich ELISA assay that allows quantitative measurement, by chemiluminescence, of several proteins per well [65]. Significant, measurable amounts of these growth factors are already present at passage one [65], which gives us an approximation of growth factor secretion by non-cultured PSC and total SVF, as compared with longer cultured PSC and ASC. For osteogenic differentiation, PSC (pre-cultured or not), SVF and ASC are cultured in the presence of ascorbic acid and beta-glycerol phosphate. Osteoblastic differentiation is detected quantitatively by real time PCR (Runx2, Osterix, osteopontin, and osteocalcin) [53], alkaline phosphatase (ALP) expression and alizarin red staining [50].

Figure 10:
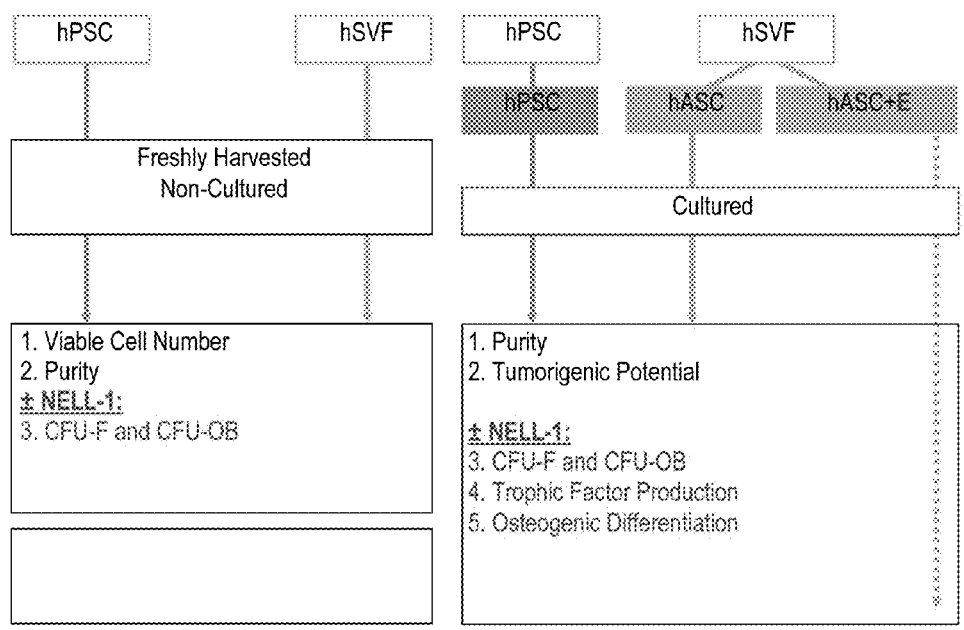
FIG. 10 shows results of in vitro studies on osteogenic differentiation experiments on purified PSC cultured in association (contact co-culture) with endothelial cells.

Another reason to use purified PSC rather than the total SVF fraction as a source of therapeutic osteogenic cells is that endothelial cells negatively regulate the differentiation potential of MSC such as ASC or BMSC [19,20] (and our unpublished results). To confirm and document these results, the same osteogenic differentiation experiments are repeated on purified PSC cultured in association (contact co-culture) with endothelial cells (E) sorted from the same fat tissue samples (FIG. 10).

Figure 11:
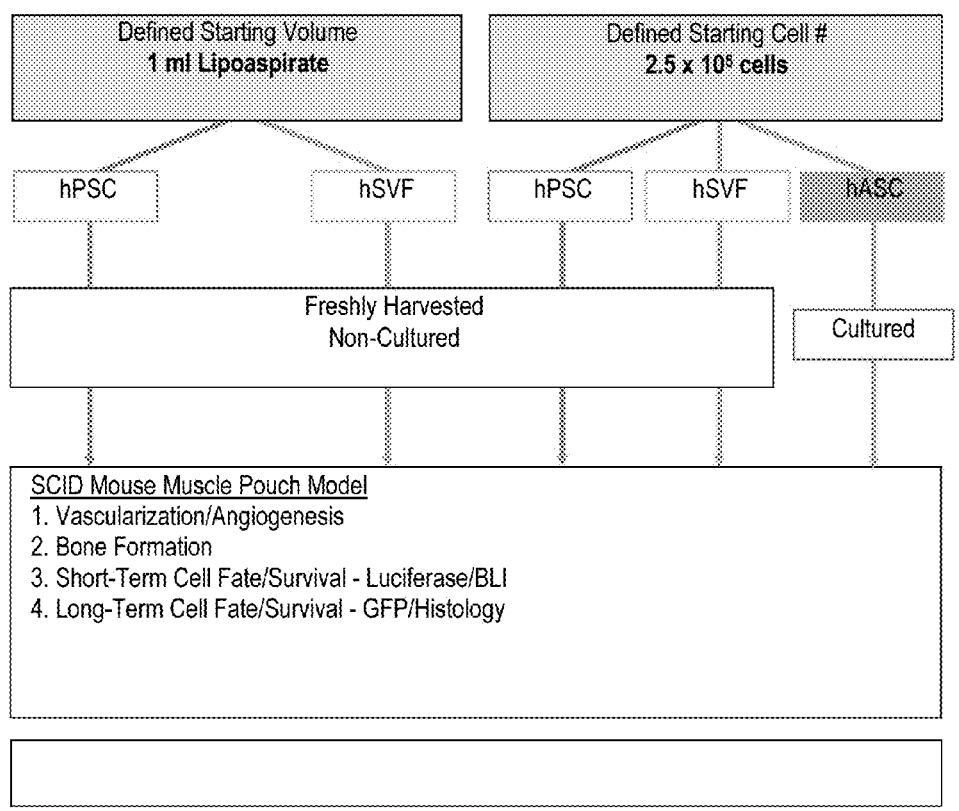
FIG. 11 shows results of in vivo studies on cell fate/survival, angiogenesis, and osteogenesis assessed after implantation in SCID mouse thigh muscle pouch.

To assay tumorigenic potential, cells are first analyzed for anchorage independent growth after plating at various densities in soft agar in proliferation medium. Colonies are counted at 2 and 3 weeks post seeding. In parallel, cells from the different populations to be assayed are seeded on a piece of Gelfoam and implanted into a skeletal muscle pocket in the hind-limb of a SCID mouse. Animals are monitored for tumor formation by physical palpation, eventually sacrificed and analyzed for the presence of tumors [70]. Karyotypes of all cell populations under study are also analyzed on fixed metaphasic chromosomes to detect possible anomalies [71]. Cell fate/survival, angiogenesis, and osteogenesis are assessed after implantation in SCID mouse thigh muscle pouch (FIG. 11, Table 2). Cells are labeled [using lentiviral luciferase or green fluorescent protein (GFP)], seeded on acellular allograft bone scaffold ±300 μg NELL-1 and implanted bilaterally in mouse biceps femoris (total volume=100 μl/side). Unless otherwise specified, all in vivo studies in this proposal utilize NELL-1 that is lyophilized onto 200-300 μm β-tricalcium phosphate carrier particles (β-TCP) of defined composition and porosity for enhanced biochemical stability (retains bioactivity for up to 3 months when stored at room temperature) and biological efficiency [72]. Both cells isolated from a defined lipoaspirate volume (1 ml) or defined cell numbers ($2.5 \times 10^5$) are tested. Human cell persistence and migration are tracked using bioluminescence imaging (BLI) and luciferase immunostaining (short term: 1-8 weeks) as well as GFP/histology (long term: 3 months). hPSC mediated vascular ingrowth and bone formation are assessed by histology (hematoxylin-eosin), histomorphometry (Masson trichrome) and immunostaining (vWF, VEGF, BSP, OCN and human MHC Class I). Quantitative bone volume/tissue volume, bone surface area/volume, mineralization density, along with trabecular thickness, number, and separation [73] are assessed by high-resolution microCT (SkyScan™; Kontich, Belgium) and analyses are performed using Skyscan™ CT Analyzer software [51].

TABLE 2

SCID Mouse Muscle Pouch Model

| Cell | Lentiviral | NELL-1 | 1 wk | 2 wk | 3 wk | 4 wk | 8 wk | 3 mo GFP |
|---|---|---|---|---|---|---|---|---|
| | | | | | SACRIFICE | | | |
| | | | | Bioluminescence Imaging (BLI) | | | | |
| DEFINED 1 ml LIPOASPIRATE VOLUME | | | | | | | | |
| hPSC | Luciferase | + | 4 mice | 4 mice | 4 mice | 4 mice | 4 mice | |
| | | − | 4 mice | 4 mice | 4 mice | 4 mice | 4 mice | |
| | GFP | + | | | | | | 4 mice |
| | | − | | | | | | 4 mice |
| hSVF | Luciferase | + | 4 mice | 4 mice | 4 mice | 4 mice | 4 mice | |
| | | − | 4 mice | 4 mice | 4 mice | 4 mice | 4 mice | |
| | GFP | + | | | | | | 4 mice |
| | | − | | | | | | 4 mice |
| DEFINED $2.5 \times 10^5$ CELL NUMBER | | | | | | | | |
| hPSC | Luciferase | + | 4 mice | 4 mice | 4 mice | 4 mice | 4 mice | |
| | | − | 4 mice | 4 mice | 4 mice | 4 mice | 4 mice | |
| | GFP | + | | | | | | 4 mice |
| | | − | | | | | | 4 mice |
| hSVF | Luciferase | + | 4 mice | 4 mice | 4 mice | 4 mice | 4 mice | |
| | | − | 4 mice | 4 mice | 4 mice | 4 mice | 4 mice | |
| | GFP | + | | | | | | 4 mice |
| | | − | | | | | | 4 mice |
| Cultured hACS | Luciferase | + | 4 mice | 4 mice | 4 mice | 4 mice | 4 mice | |
| | | − | 4 mice | 4 mice | 4 mice | 4 mice | 4 mice | |
| | GFP | + | | | | | | 4 mice |
| | | − | | | | | | 4 mice |
| Total Animals Used | | | 240 Mice (2 implants per animal) | | | | | |

If in some embodiments, quantitative assessment of PSC vs. ASC can be required in terms of developmental potential, differentiation into myotubes can be tested in vitro as previously performed [70]. The exemplary cell seeding density ($2.5 \times 10^5$/100 μl) and NELL-1 dose (100-300 μg; 1.0-3.0 mg/ml) are identical to those used in our test data demonstrating successful cell survival, bone formation, and vascular ingrowth (data not shown). We have also determined that 100 ml SVF yields ~$2.3 \times 10^7$ cells, of which ~24% (~$1.2 \times 10^7$ cells) are PSC (Table 1). Thus, the use of "1 ml" as the "defined lipoaspirate volume" is within range to provide sufficient cell numbers (~$10^5$) for osteogenesis. If needed, in some embodiments, we can alter the defined volume, cell number, or NELL-1 dose to further enhance bone formation.

2. Studies on hPSC+NELL-1 Formulations in Rodent Bone Formation

Based on safety and efficacy endpoints, the hPSC+ NELL-1 formulation is further compared with BMP2+ Helistat® collagen sponge (INFUSE® Bone Graft) and gold standard "autologous" bone graft for safety and efficacy in normal and impaired [e.g., ovariectomized (OVX)] bone regeneration models. These studies show that the hPSC+ NELL-1 product is more or as efficacious and safe as BMP2 or autologous bone graft.

Methods and Techniques

For initial formulation of the therapeutic product, systematic studies on hPSC density ($PSC^{OPT}$) and NELL-1 dose ($NELL-1^{OPT}$) are performed. First, luciferase tagged hPSC are implanted in a biocompatible carrier at three densities ±NELL-1 (300 µg total dose; 3.0 mg/ml) in SCID mice (Table 3).

TABLE 3

SCID Mouse Muscle Pouch Model (100 µl Total Volume)

| DETERMINE OPTIMAL CELL # ($hPSC^{OPT}$) FOR SF | | | SACRIFICE | | | |
|---|---|---|---|---|---|---|
| | | | 1 wk | 2 wk | 3 wk | 4 wk |
| Cells | Cell # | NELL-1 | Bioluminescence Imaging | | | |
| Fresh hPSC (Luciferase tagged) | $2.5 \times 10^4$ | + | 4 mice | 4 mice | 4 mice | 4 mice |
| | | − | 4 mice | 4 mice | 4 mice | 4 mice |
| | $2.5 \times 10^5$ | + | Performed in Aim 1A | | | |
| | | − | | | | |
| | $2.5 \times 10^6$ | + | 4 mice | 4 mice | 4 mice | 4 mice |
| | | − | 4 mice | 4 mice | 4 mice | 4 mice |
| Total Animals Used | | | 64 Mice (2 implants per animal) | | | |

The effect of NELL-1 on hPSC persistence, hPSC mediated vascular ingrowth and bone formation at the various densities are assessed. The hPSC density demonstrating the most optimal BLI signals and bone growth are designated $hPSC^{OPT}$. Second, we test GFP tagged $hPSC^{OPT}$ at the maximum concentration of 3.0 mg/ml, as well as 1.5 and 0.75 mg/ml in an athymic rat SF model that normally fuses at 4 weeks with non-cell based NELL-1 (Table 4).

TABLE 4

| DETERMINE OPTIMAL NELL-1 DOSE ($NELL-1^{OPT}$) | | | Athymic Rat Spine Fusion (SF) Model (300 µl Total Volume) | | |
|---|---|---|---|---|---|
| | Total Dose | Concentration | SACRIFICE | | |
| Cells | NELL-1 | NELL-1 | 2 wk | 3 wk | 4 wk |
| Fresh $hPSC^{OPT}$ (GFP tagged) | 900 µg | 3.0 mg/ml | 4 rats | 4 rats | 4 rats |
| | 450 µg | 1.5 mg/ml | 4 rats | 4 rats | 4 rats |
| | 225 µg | 0.75 mg/ml | 4 rats | 4 rats | 4 rats |
| | No NELL-1 (Control) | | 4 rats | 4 rats | 4 rats |
| No hPSC (Control) | 900 µg | 3.0 mg/ml | 4 rats | 4 rats | 4 rats |
| Total Animals Used | | | 60 Rats (1 SF/animal) | | |

The NELL-1 dose demonstrating the most vascularization and bone growth with hPSC are designated $NELL-1^{OPT}$. The optimized formulation for spine fusion efficacy ($PSC^{OPT}$+$NELL-1^{OPT}$) are directly compared to BMP2/collagen (IN-FUSE® Bone Graft) and fresh rat bone graft in normal or OVX [74] skeletally mature, athymic rats (Table 5). Because syngeneic athymic rats are not available, we use allogeneic athymic donors.

TABLE 5

Athymic Rat Spine Fusion (SF) Model (300 µl Total Volume)

| COMPARE $hPSC^{OPT}$ + $NELL-1^{OPT}$ WITH CURRENT THERAPY | SACRIFICE | | | | | |
|---|---|---|---|---|---|---|
| | Normal Rat | | | OVX Rat | | |
| Treatment Groups | 2 wk | 3 wk | 4 wk | 4 wk | 6 wk | 8 wk |
| Fresh $hPSC^{OPT}$ + $NELL-1^{OPT}$ | 6 rats | 6 rats | 6 rats | 6 rats | 6 rats | 6 rats |
| BMP2 + Collagen Sponge | 6 rats | 6 rats | 6 rats | 6 rats | 6 rats | 6 rats |
| Fresh Bone Graft | 6 rats | rats | 6 rats | 6 rats | 6 rats | 6 rats |
| Total Animals Used | 108 Rats (1 SF per animal) | | | | | |

Efficacy and safety are evaluated by imaging, surgical pathology, histology, immunohistochemistry, and cell tracking studies as described above. Biomechanical testing is also performed. Anti-murine antibodies (from FACS) or anti-NELL-1 are detected by ELISA. Immunostaining for osteoblastic, chondrogenic, and adipogenic cell markers such as RUNX2, SOX9, collagen II and X, or PPARγ is performed. Because both OVX and BMP2 promote osteoclastogenesis [39], tartrate-resistant acid phosphatase (TRAP) staining is performed to asses osteoclast activity (a potential safety issue as excessive osteoclast activity can cause vertebral subsidence). Bone mineral loss in OVX animals is assessed by dual x-ray absorptiometry (DEXA).

Figure 7:
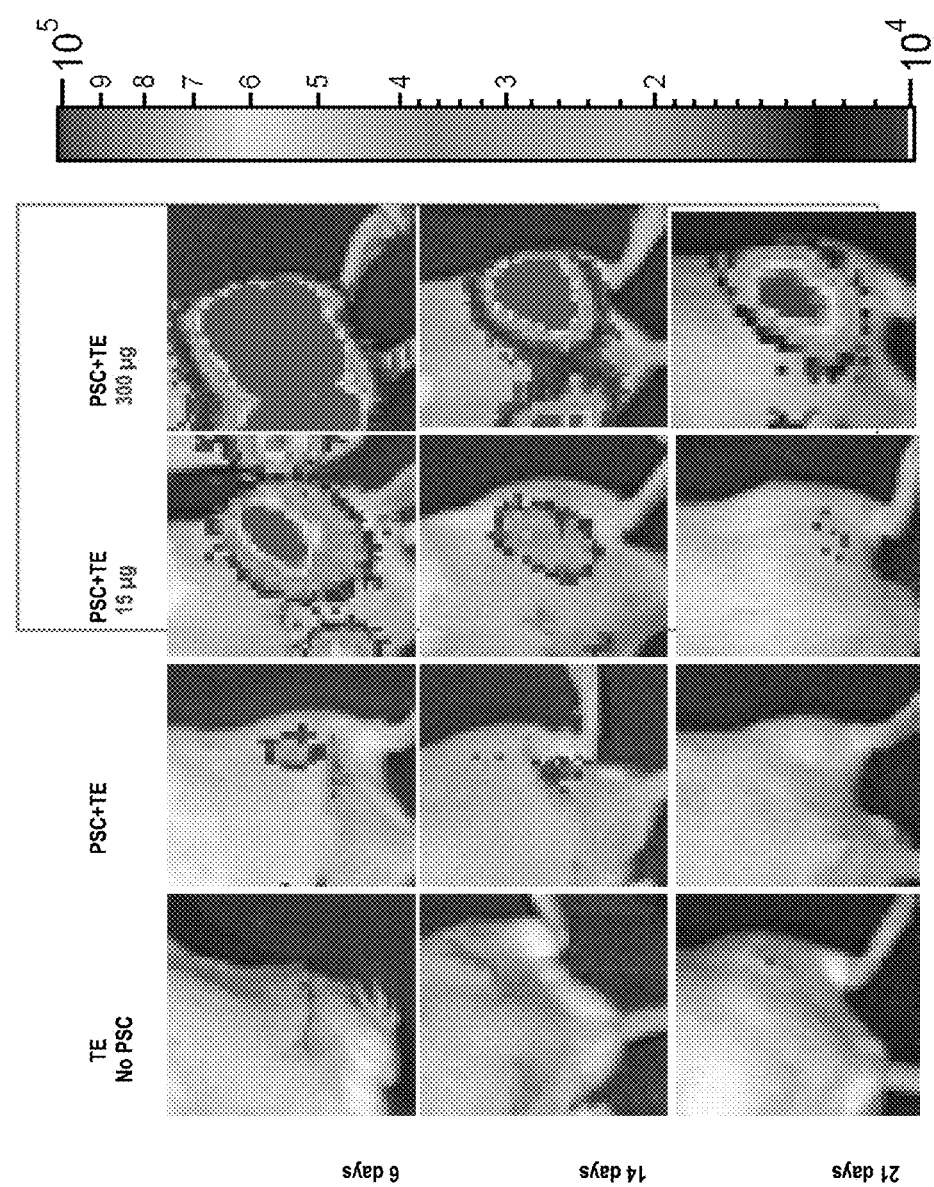
FIG. 7 shows bioluminescence imaging of implanted human PSC. SCID mice (n=4 in each group) were implanted intramuscularly with TE®±$2.5\times10^5$ PSC±15 or 300 μg NELL-1/TCP in 100 μl total volume. No luciferase detected in PSC-free controls.
Figures 8A, 8B, 8C, 8D:
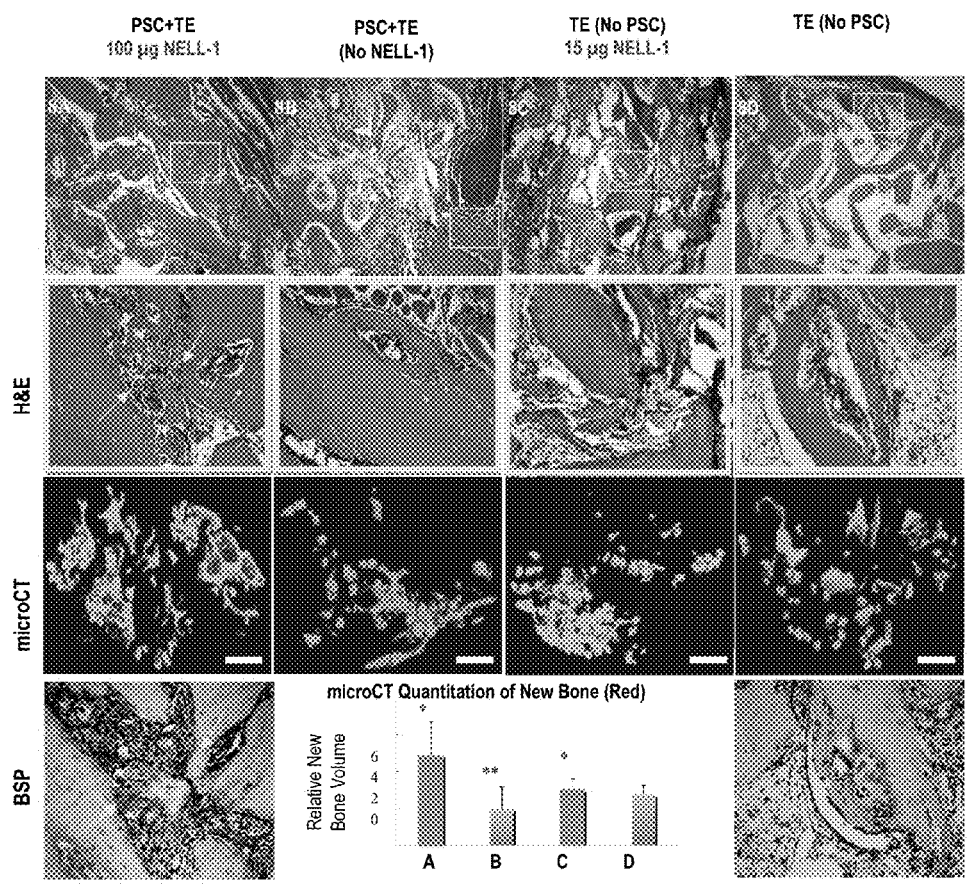
FIG. 8 shows results on PSC+NELL-1 at 4 weeks post implant. SCID mice were implanted with TE®±$2.5\times10^5$ PSC±NELL-1/TCP in 100 μA volume. Relative to TE® (D), note the abundant new bone formation in the PSC+NELL-1 group (A) (red areas in microCT) with increased bone sialoprotein (BSP) staining (arrows) and bony consolidation of the TE® particles and marrow space formation (H&E, arrows). Note the sparse cellularity and less active bone formation in the TE® only group (D). =P<0.05 higher vs. TE® only group (D); =P<0.05 lower vs. TE® only group (D).

In some embodiments, cell seeding densities and NELL-1 doses can be varied to achieve hPSC osteoinduction. Exemplary hPSC densities are from $2.5 \times 10^4$ to $10^6/100$ µl and are within range of published reports demonstrating successful MSC-mediated bone formation with larger implant volumes and/or diffusion distance in sheep [75,76,77], goat [78] and humans [79] (also reviewed in [14]). With respect to NELL-1 dosing, NELL-1 at 3.0 or 1.0 mg/ml more effectively stimulated hPSC survival or bone formation, respectively, in SCID mouse muscle pouch than 0.15 mg/ml (FIGS. 7 and 8). Meanwhile, non-cell based NELL-1 induces non-human primate spinal interbody fusion at a dose of 1.7 mg/ml in 400 µl (total dose=680 µg) at 3 months (not shown). An example of NELL-1 formulations, lyophilized NELL-1 on β-TCP carrier, provides a 40% burst release in the initial 24 hours followed by a 45% slow release over two weeks [72] and has successfully induced spine fusion in rat, sheep, and NHP models. However, non-cell based NELL-1 relies on NELL-1 diffusion from the scaffold or cell migration to the scaffold to come in contact with NELL-1. In the present invention, because the hPSC are in closer proximity to NELL-1, initial NELL-1 burst release is not required and fusion may be achieved with the use of non-burst release carriers and reduced NELL-1 dose.

4. Studies on cPSC+NELL-1 Efficacy in Bone Formation in Comparison with BMP2 or Autologous Bone Graft The studies show that that the cPSC+NELL-1 product is more or as efficacious and safe as BMP2 or autologous bone graft.

Methods and Techniques

A human device previously used in sheep and monkey spine studies is implanted in a canine model of spine fusion. There is a species-specific dose escalation to achieve fusion using BMP2 [80] and NELL-1. Since dog and sheep have similar dose ranges, the 0.6 mg/ml NELL-1 dose that was effective in sheep is used. Spine fusion efficacy of non cell based NELL-1 in dogs at 0.6 mg/ml+acellular allograft bone carrier with 2 lumbar implants per animal (N=6 NELL-1 and N=6 No NELL-1 control implants) can be performed as control. GFP tagged cPSC at 5-fold above and 5-fold below the hPSC$^{OPT}$ density with two different NELL-1 doses and saline controls (N=4 in each group; total N=36 implants) can be tested. The GFP tagged cPSC$^{OPT}$+NELL-1$^{OPT}$ can then be tested with BMP2 (INFUSE® Bone Graft) and autograft bone (N=6 in each group; total N=18 implants).

5. Examples of Osteoinduction Studies

Isolation of 1-Perivascular Stem Cells

Figure 2A:
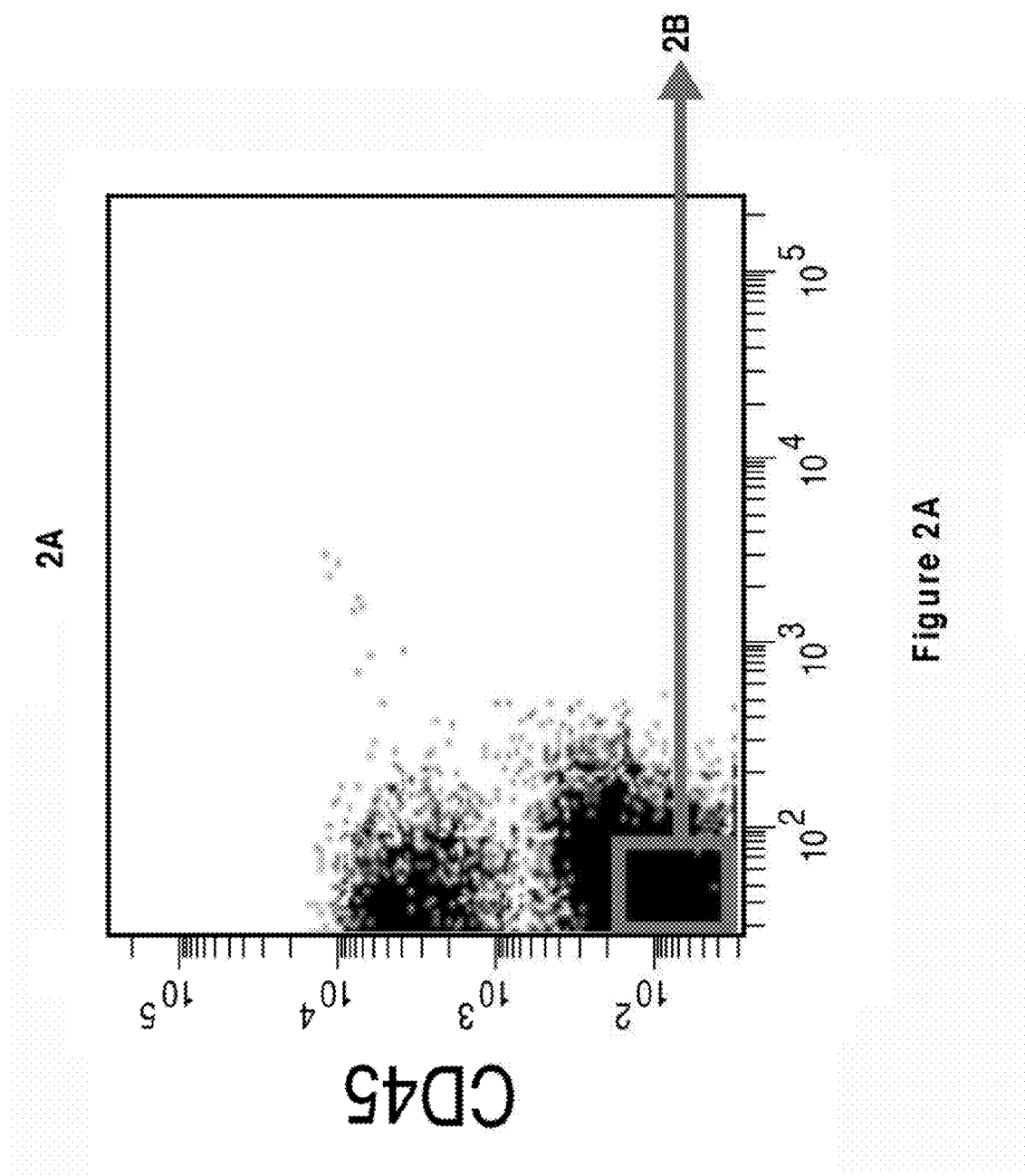
FIGS. 2A-2F show adventitial MSC. (A,B) Pericytes were sorted from adipose tissue (red), as well as CD146–CD34$^{hi}$ cells (green), also endowed with stem cell potential. (C) CD146–CD34$^{high}$ cells were further divided into CD31+ and CD31– cells, only the latter gave rise to MSC. Sorted CD146–CD34$^{high}$CD31– cells (x) are not contaminated by endothelial cells or pericytes (D). (E) CD146–CD34$^{hi}$CD31– cells (arrows) are all localized in the tunica adventitia of larger blood vessels (CD34 in red). (F) Purified adventitial MSC are osteogenic in vitro (alizarin red staining)
Figures 2B, 2C:
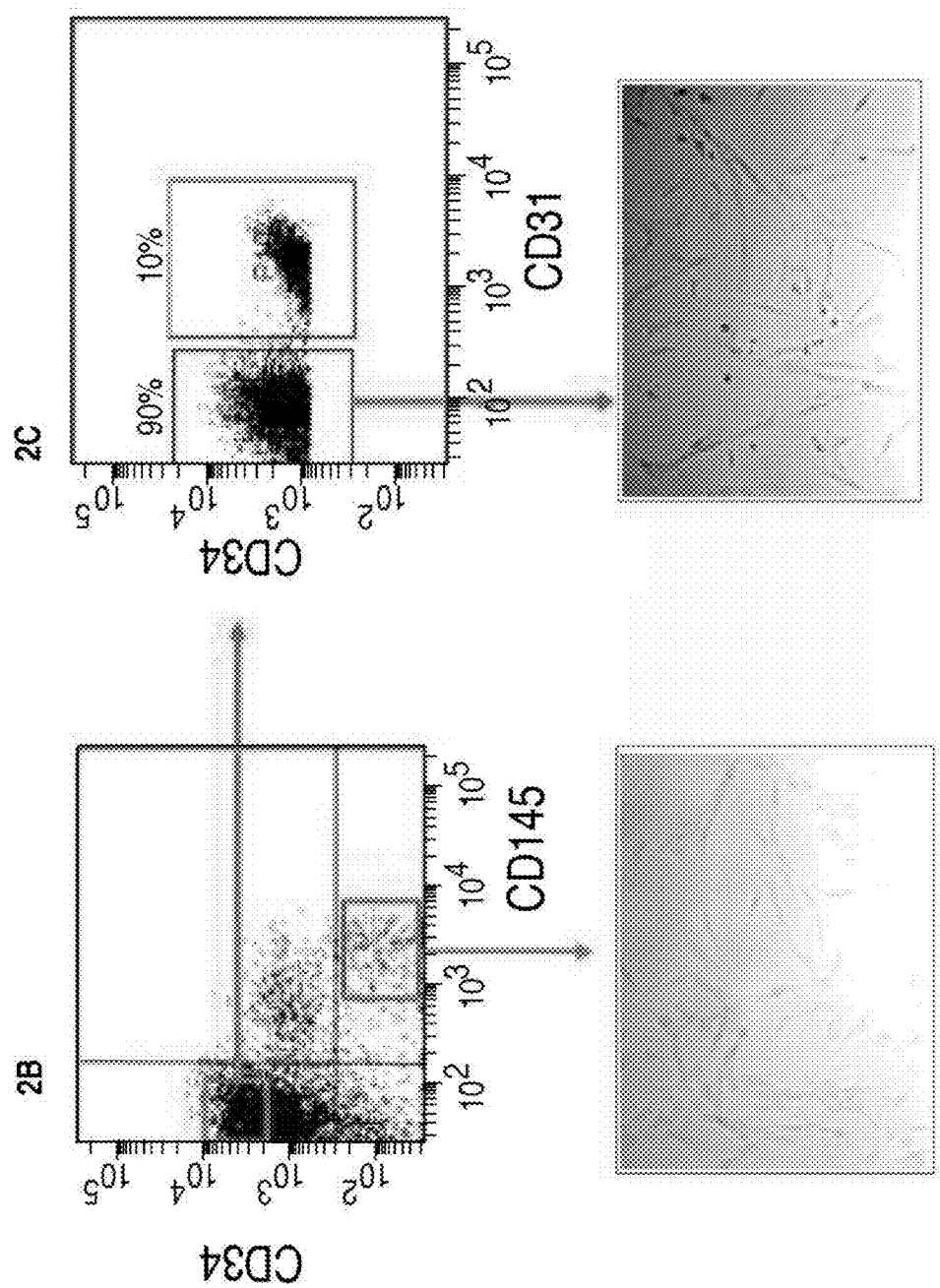
Figure 2D:
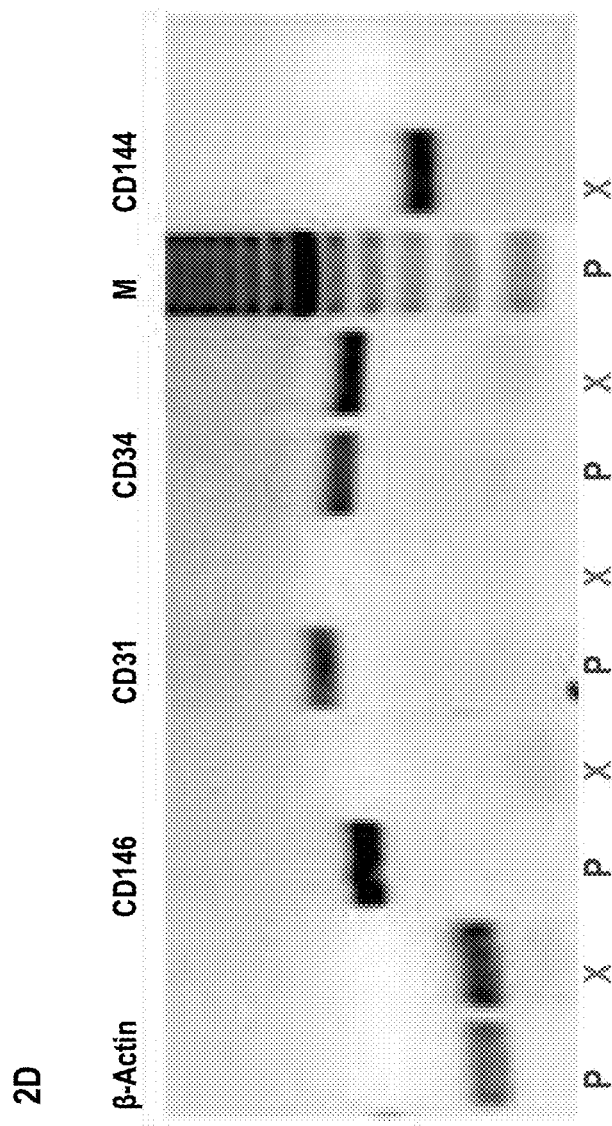
Figure 2E:
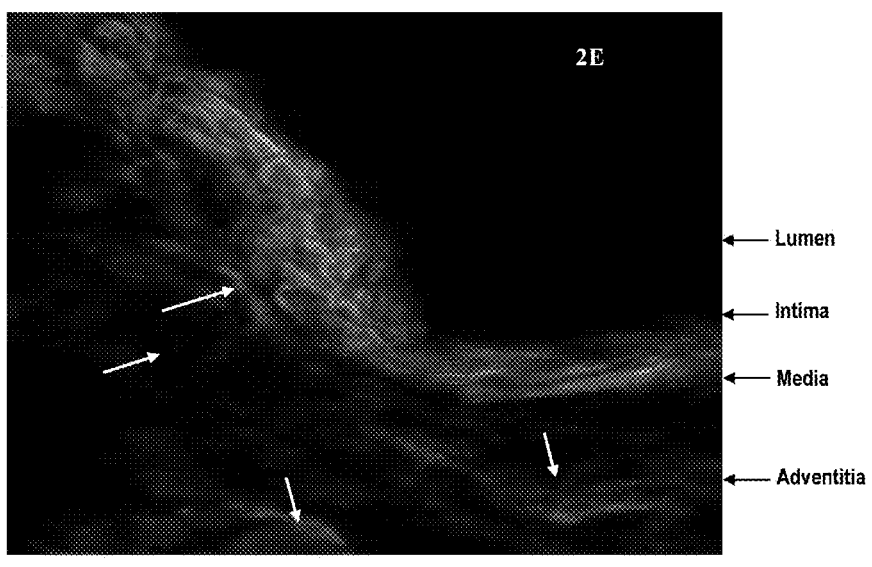
Figure 2F:
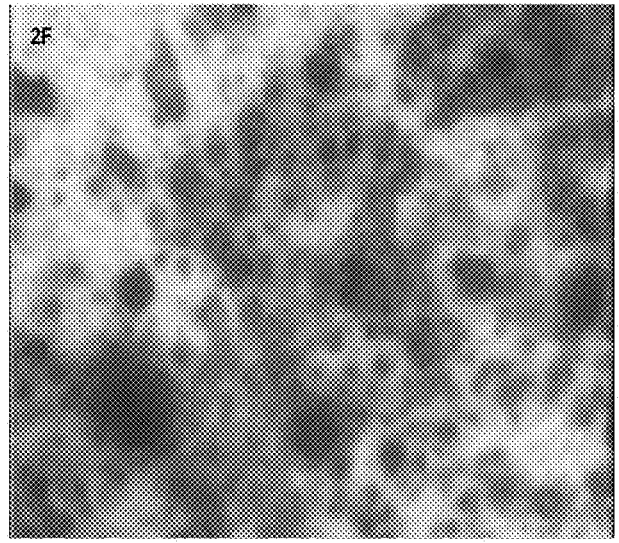
Figures 3A, 3B, 3C, 3D, 3E, 3F:
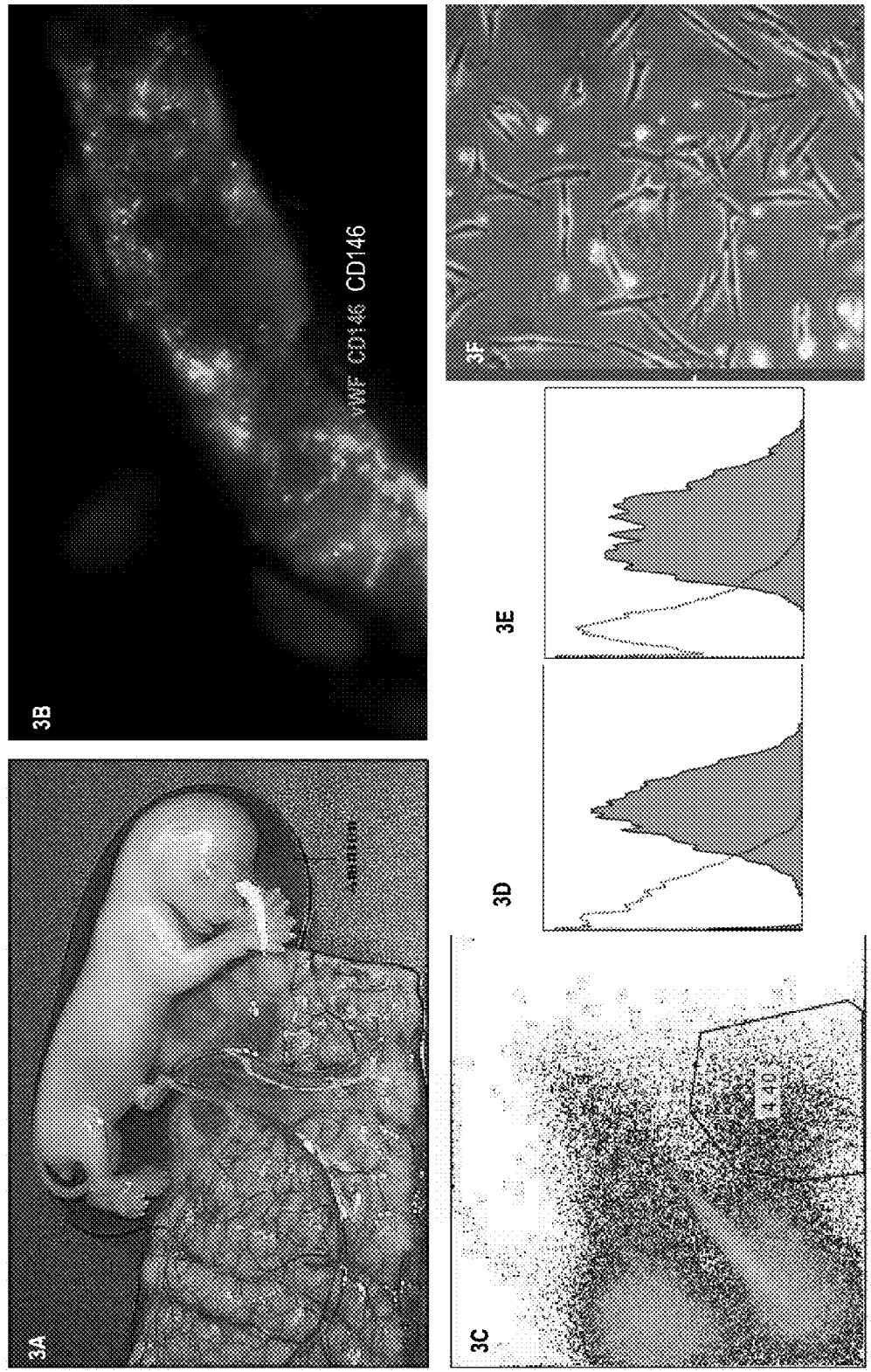
FIGS. 3A-3F show dog pericytes. The placenta (A) was used as a source of canine pericytes. vWF+ endothelial cells are encircled by CD146+ pericytes (B). As for human cells, canine pericytes were sorted as CD146+CD34– cells (gate in C; compare with FIG. 1E), coexpress CD90 (D) and CD44 (E) and were established in long-term culture (F)

We have prospectively identified vascular pericytes in multiple human organs and shown that these cells are mesodermal progenitors that give rise to MSC in culture [36,81]. Pericytes can differentiate into cartilage, fat, skeletal muscle and bone cells (FIGS. 1A-1G), but also secrete multiple growth factors, which likely explains in part their robust regenerative potential [29]. However, non-pericyte cells (outside the red gate in FIG. 1E), were also found to include MSC progenitors. Further partition revealed that this MSC potential is confined within CD34high CD31− (non-endothelial) cells (FIG. 2C), all found in the tunica adventitia of arteries and veins (FIG. 2E). Sorted adventitial MSC differentiate in culture into cartilage, bone (FIG. 2F) and fat cells, and into myofibers after injection into the SCID mouse muscle.

In summary, two categories of perivascular cells, pericytes and adventitial cells, named collectively perivascular stem cells (PSC), account for the origin of MSC in all human tissues tested. PSC natively express MSC markers, are multipotent, and upon culture exhibit the shape, growth characteristics, migratory properties, developmental potential and functions, including immunomodulation and hematopoiesis support, of conventional MSC. Importantly, PSC contain the whole potential to give rise to MSC.

Several antibodies to markers used to characterize human PSC (vWF, CD34, CD44, CD90, CD146 and NG2) cross-react with the canine homologs. We have characterized pericytes in the dog placenta; FACS purification and culture of these cells revealed characteristics similar to those of human pericytes (FIGS. 3A-3F).

PSC Yields from Lipoaspirates

Our data on PSC yields from the stromal vascular fraction (SVF) of human lipoaspirates agrees with published adipose derived stem cell (ASC) yields assessed by the CFU-F assay (~$10^6$ stem cells/100 ml) [15,26,27] (Table 1). BMSC seeding densities in the 2.5×$10^5$ to $10^7$/ml range successfully regenerated bone in large animals and humans [75,76,77,78,79] (reviewed in [14]). With typical cosmetic lipoaspirate volumes of 2 L [82], containing at least $10^6$ viable PSC/100 ml, clinically relevant PSC numbers are readily obtained without culture. Notably, cell viability is higher in PSC than total SVF populations. Thus, sorted PSC should be advantaged over total SVF implants because all non-viable cells are excluded.

TABLE 1

| | Per 100 cc Lipoaspirate | | |
|---|---|---|---|
| # Total SCF cells | # Viable Cells in SCF | # PSC in SVF | # Viable Cells in PSC |
| 5.0 ± 2.5 × $10^7$ | ~2.3 × $10^7$ (46% ± 4.7%) | ~1.2 × $10^7$ (24% ± 3.5%) | ~0.8 × $10^7$ (67% ± 18%) |

NELL-1, an Osteospecific, Osteoinductive Growth Factor

Non-Cell Based Bone Regeneration:

NELL-1+ allograft reproducibly induced bone regeneration in various small animals [50,53,54,55] as well as in interbody spinal fusion in sheep [56] and monkeys (not shown). In sheep, NELL-1 in an allograft bone scaffold achieves comparable fusion as the BMP2 (INFUSE®) group without the cyst formation seen with BMP2 (not shown).

NELL-1 Inhibits Adipogenesis:

NELL-1 significantly reduces endogenous and BMP2 induced expression of the major adipogenic transcription factors [2] PPARγ and CCAAT/enhancer binding protein in primary rat BMSCs (not shown). In addition, NELL-1 markedly induces osteoblastogenesis and suppresses BMP2 induced adipogenesis in implanted goat BMSC [11].

Figure 4:
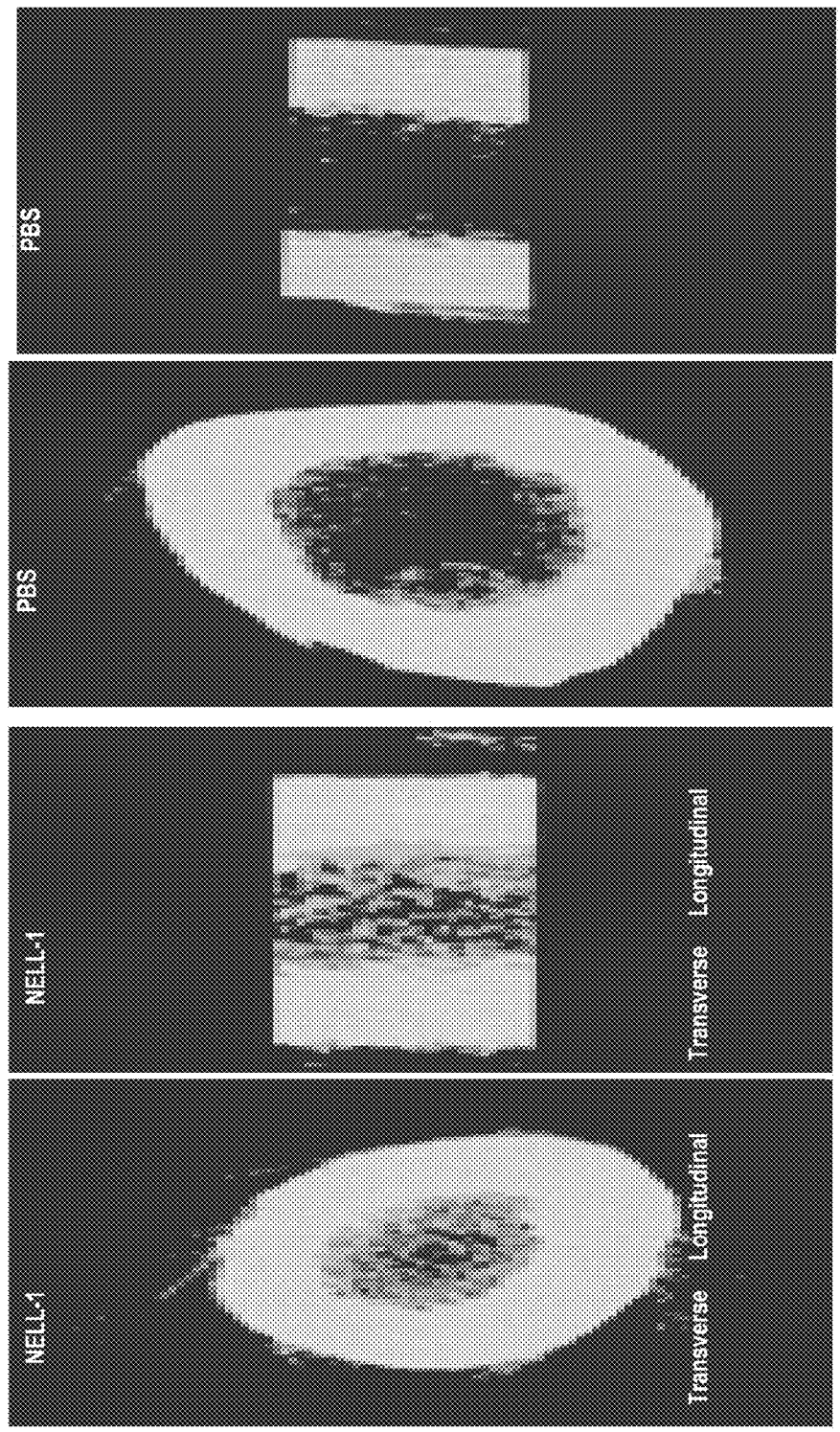
FIG. 4 shows 2 week microCT sections of rat femur. 200 μg NELL-1/TCP, or saline/TCP (control) were injected through a trepanation defect into the rat femur.

NELL-1 Effects on Stem Cells in Situ:

NELL-1 significantly increased the number of Stro-1+ cells (MSC related bone marrow stromal cells [83]) and bone sialoprotein (BSP, an osteoblast marker) expression in rat vertebral bodies (not shown). Accordingly, direct NELL-1/β-TCP carrier injection into the rat femur increases bone volume and marrow density (FIG. 4).

Figure 5:
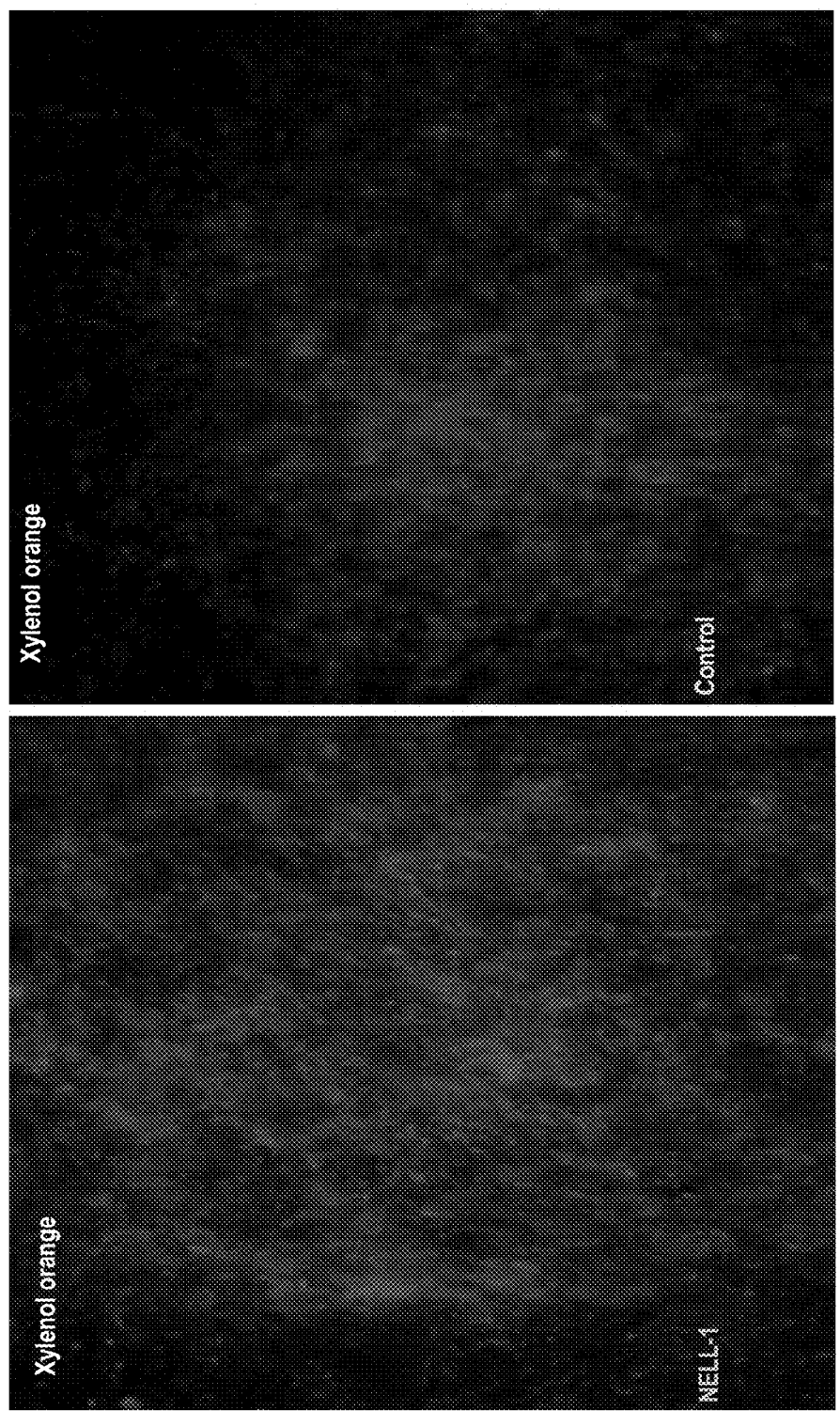
FIG. 5 shows NELL-1 increases human PSC mineralization. PSC were cultured for 9 days±300 ng/ml NELL-1, then stained with xylenol orange fluorochrome.

NELL-1 Effects on PSC In Vitro:

When added to PSC under osteogenic conditions NELL-1, 1—significantly increased xylenol orange uptake (a mineralization marker) (FIG. 5) and 2—also significantly increased mRNA levels of the osteoblastic cell markers RUNX2, osterix (OSX), and osteocalcin (OCN), decreased PPARγ, and increased VEGF (not shown). NELL-1 thus potently promotes PSC osteogenic and angiogenic activities.

The PSC+NELL-1 Development Candidate—Comparison with Trinity® Evolution™ (TE®)

Figure 6:
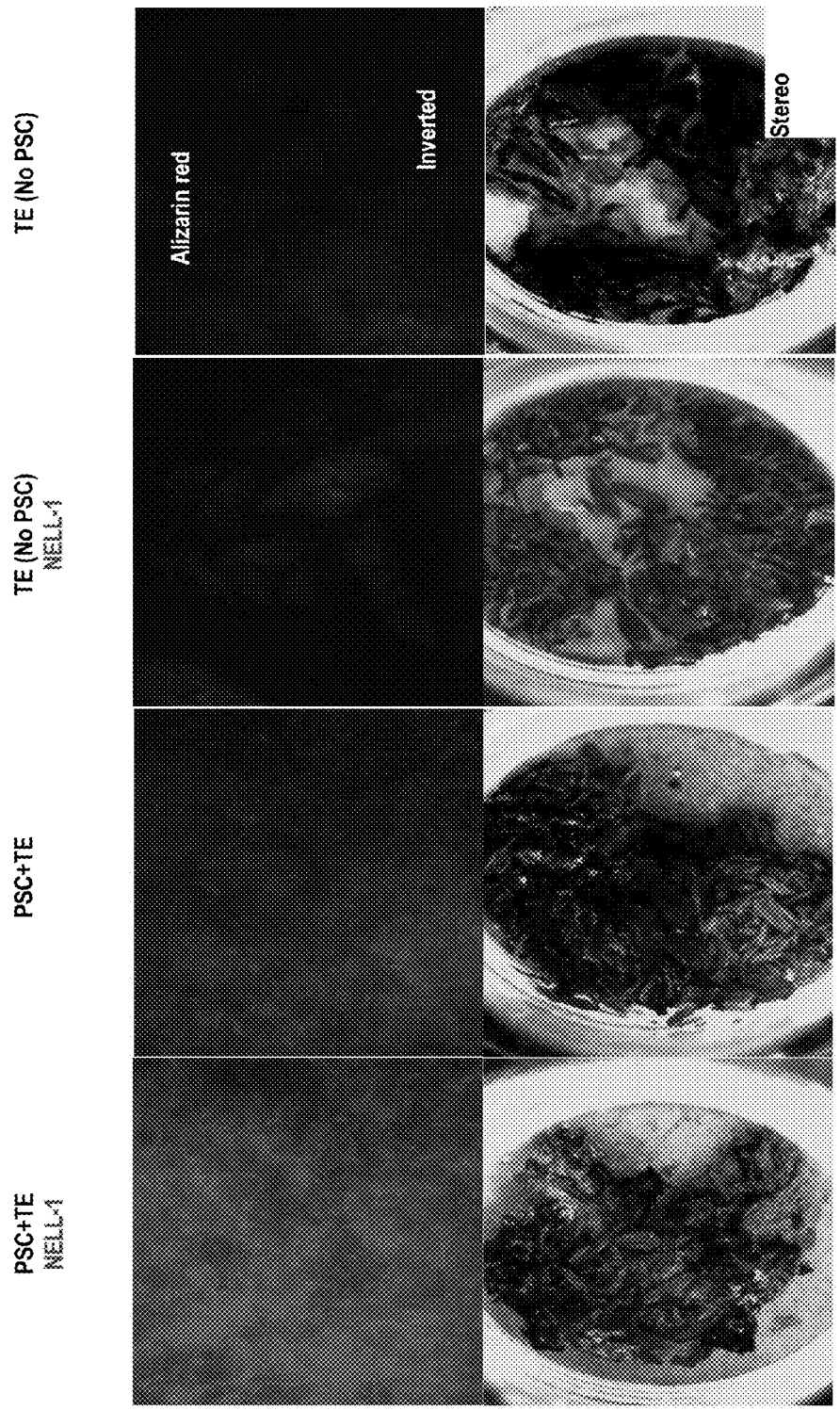
FIG. 6 shows In vitro mineralization of PSC+NELL-1 on TE®. 100 μl of TE®±300 ng/ml NELL-1 or TE® loaded with $2.5\times10^5$ PSC±300 ng/ml NELL-1 were placed in 24-well plate inserts under osteogenic conditions for 12 days. Mineralization (alizarin red) assessed using inverted (top) or stereo (bottom) fluorescence microscopy.
Figures 9A, 9B, 9C, 9D, 9E, 9F:
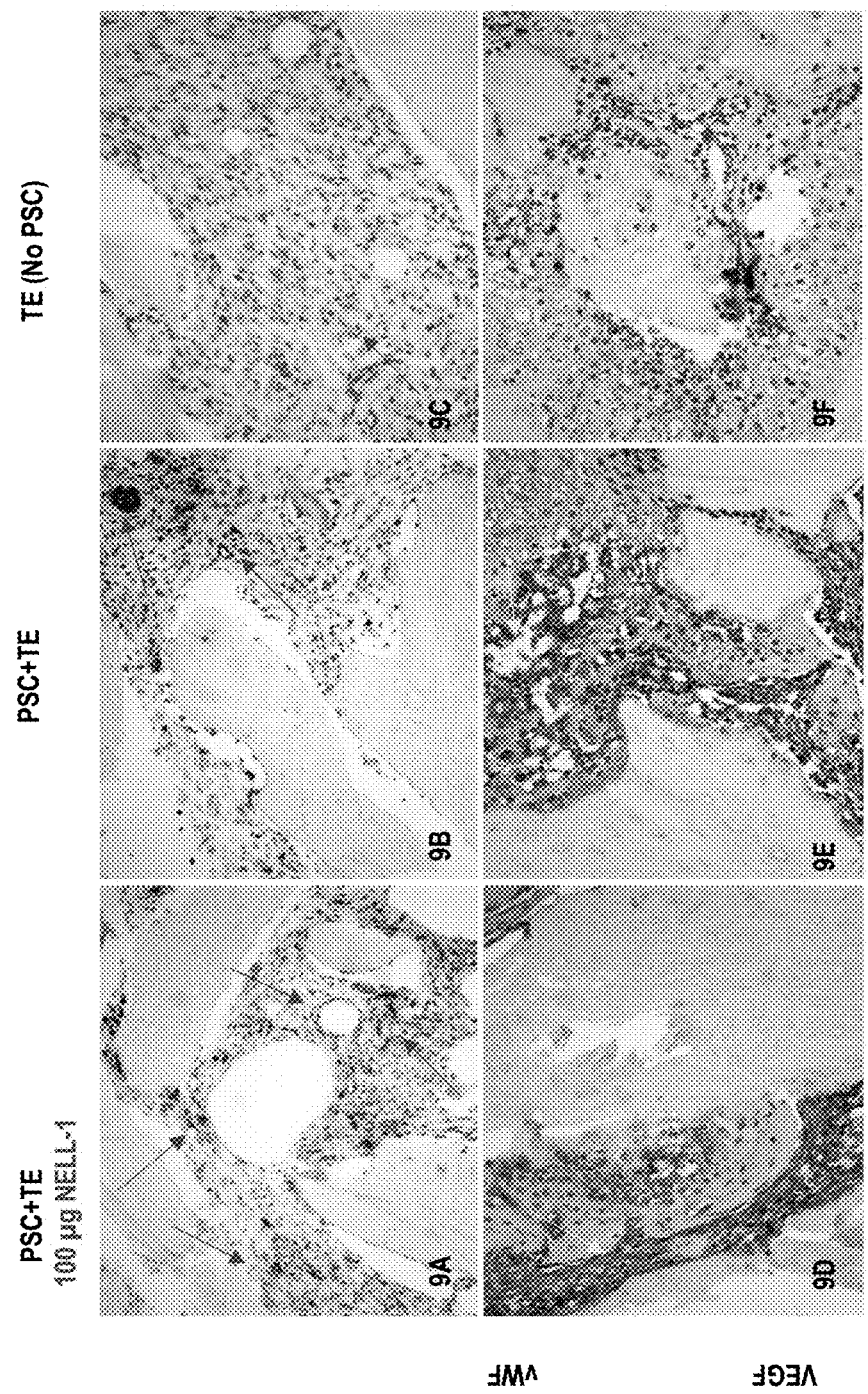
FIG. 9 shows results on angiogenesis in PSC+NELL-1 grafts. SCID mice were implanted per FIG. 8. Immunostaining of 1 week (A-C) and 2 week (D-F) specimens show increased endothelial vWF (A,B-red arrows) and significantly increased VEGF (D,E-yellow arrows) in PSC groups relative to TE®. Anti-human MHC I (H300) staining was also increased in PSC groups, indicating persistence of PSC (not shown).

TE® is a FDA-regulated, cryopreserved allograft bone containing "viable adult stem cells and osteoprogenitor cells" [7]. We investigated the osteogenic properties of TE® alone compared to TE® used as a scaffold for PSC, NELL-1, or PSC+NELL-1. When cultured in osteogenic medium, minimal mineralization was seen in TE® or TE®+NELL-1, indicating that TE® contains few osteogenic cells (FIG. 6). In contrast, introduction of PSC increased mineralization, which was further increased by PSC+NELL-1, indicating that adequate numbers of appropriate stem cells (PSC) and NELL-1 are required for maximal mineralization (FIG. 6). Moreover, NELL-1 applied to luciferase tagged PSC+TE® implanted in SCID mouse muscle significantly increased luciferase intensity (FIG. 7); thus NELL-1 promotes PSC survival and/or proliferation. Histological and microCT examination of the SCID mouse implant groups revealed the least bone formation in the TE® and, interestingly, in the PSC+TE® groups (suggesting that NELL-1 is indeed important for in vivo PSC survival or activity) (FIG. 8). Notably, at 4 weeks the PSC+TE®+NELL group exhibited the most bone formation as well as marked BSP expression in a NELL-1 dose-dependent fashion (FIG. 8). Relative to TE®, PSC+TE® induced significantly more endothelial vWF staining in granulation tissue at one week (not shown) and markedly increased VEGF expression at 2 weeks with the effect further augmented by NELL-1 (FIG. 9). PSC are therefore angiogenic, trophic, and osteogenic in the presence of NELL-1. Tagged PSC were still visible at 4 weeks in areas of active mineral deposition and along vessels (not shown). In summary, these data show that i) PSC mineralize and form bone under appropriate environments, ii) NELL-1 is a potent osteospecific, osteoinductive molecule that promotes stem cell function while inhibiting adipogenesis, iii) NELL-1 increases PSC proliferation and/or survival, and iv) PSC+NELL-1+TE® forms more bone than TE® alone or TE®+PSC. Overall, these data demonstrate the usability and efficacy of PSC+NELL-1 to promote bone formation and vascular ingrowth.

Summary

From our data, we have developed methods to extract adequate quantities of human PSC (hPSC) from lipoaspirate to support cell-based tissue engineering without ex vivo expansion. We have documented hPSC identity, purity and potency [36,68], and demonstrated the trophic, immunomodulatory, hematopoiesis supporting, angiogenic and osteogenic potentials of hPSC[1-4] (and unpublished results). Importantly, we show superior bone forming efficacy with hPSC+NELL-1 relative to hPSC or NELL-1 alone. Because NELL-1 is currently at the pre-IDE/IND stage for a non-cell based lumbar spinal fusion indication, we have already developed cGMP compliant NELL-1 manufacturing and detailed the mode of action data on NELL-1 osteoinductivity and NELL-1 release data from various 510 (k) approved biocompatible materials for bone regeneration. Therefore, we believe that starting IND-enabling studies in three years is realistic. The seven subaims in this proposal are designed to achieve five milestones needed (interspersed at months 9, 18, and 36) before starting IND-enabling studies.

Example 2. Isolation of Adventitia PSC from Liposuction Aspirate

SVF Isolation from Liposuction Aspirate.

Liposuction aspirate was washed with an equal volume of PBS and centrifuged for 10 minutes at 400×g. After centrifugation, the top layer of the preparation, representing the tissue fraction containing the SVF, was collected and further washed in PBS. The tissue fraction was then enzymatically processed by addition of an equal volume of digestion solution (DMEM, collagenase II 1 mg/ml, DNAse 10 µg/ml, 1% Pen-Strepto, 3% BSA) and incubation for 45 minutes at 37 C under agitation (250 rpm). The enzymatic digestion was stopped after addition of PBS 5 mM EDTA and the solution was filtered through 100 µm cell strainer. After two washes in PBS 5 mM EDTA and centrifugation at 400×g for 10 minutes, the supernatant containing adipocytes was discarded and the pellet was resuspended in 10 ml red blood cell lysis buffer for 10 minutes at room temperature. The suspension was washed in PBS 5 mM EDTA and centrifuged at 400×g for 10 min. The pellet containing the SVF was resuspended in DMEM 10% FBS prior to cell count, culture and staining with specific antibodies for the purification of PSC via FACS sorting.

SVF Culture and CFU-F Assay

Conventional MSC-like adipose stem cells (ASC) was isolated by plating $10^7$ unfractionated SVF cells per well in a 6 multiwell plate. CFU-F assay was performed for the determination of the frequency of ASC by limiting dilution of total unfractionated SVF cell plated at the increasing density of $10^2$ to $10^6$ cells per well in a 6 multiwell plate. After 2 weeks of culture, plates were stained with May Grunwald/Giemsa and the number of colonies was scored.

Detection of PSC Within the Liposuction-Derived SVF

Three hundred thousand SVF cells were washed and re-suspended in 100 µl of PBS before incubation at 4 C for 20 minutes with DAPI for the exclusion of dead cells and with the following antibodies: CD45, CD34, CD31, CD146. Cells were then washed and resuspended in PBS prior to flow cytometry analysis. After exclusion of dead cells and CD45+ hematopoietic cells, PSC are identified as CD146+ CD34− pericytes and CD34+CD31−CD146− adventitial cells. Endothelial cells are instead defined as CD34+ CD146+CD31+ cells. The same staining procedure was used for the isolation of PSC via FACS sorting. Purified PSC were resuspended in EGM2 medium and plated in 0.2% gelatin coated wells at the density of $2\times10^4$ cells per cm$^2$. CFU-F assay were performed as above described.

Example 3. Osteogenic Studies on Pericytes and NELL-1

Figure 12:
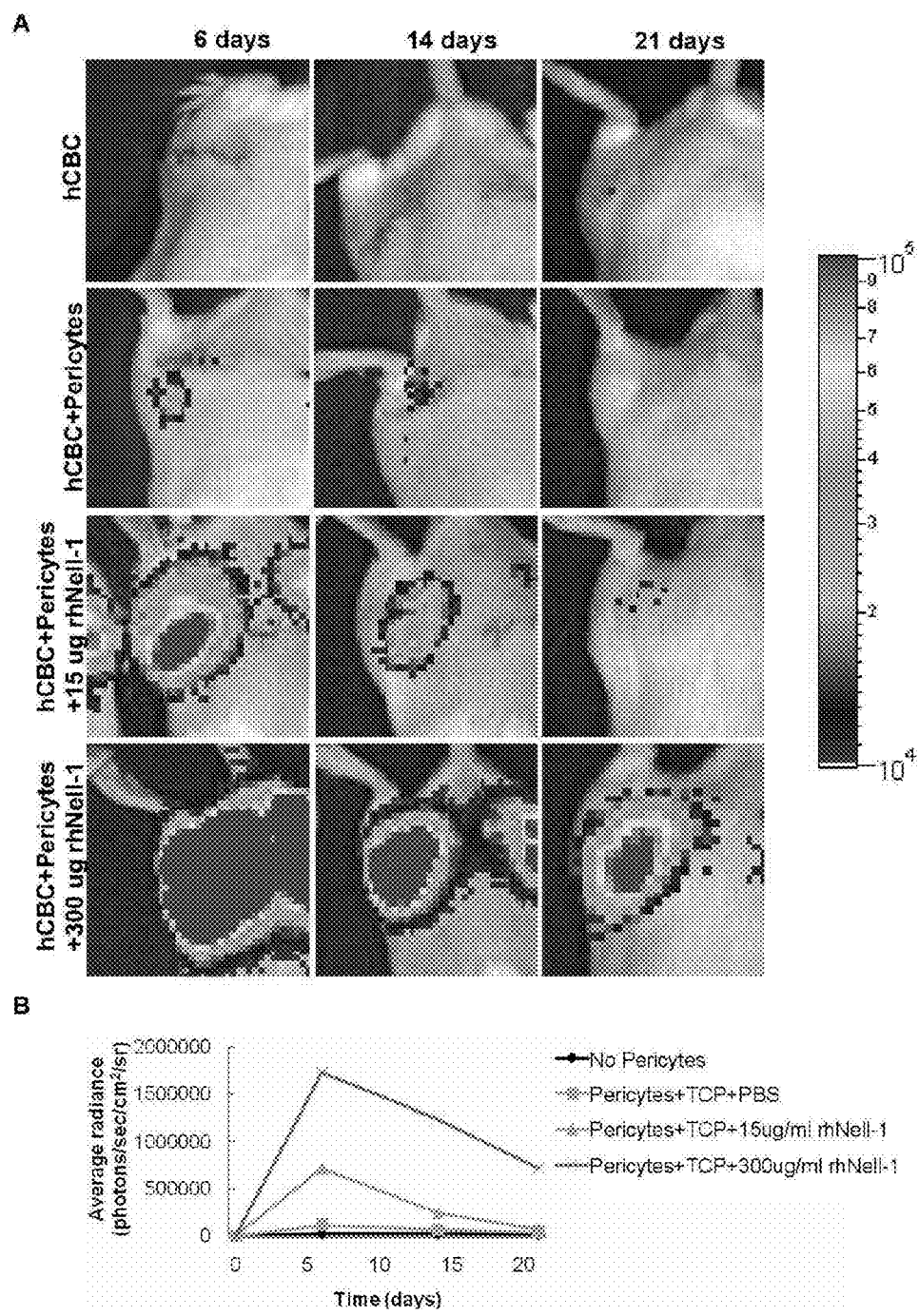
FIG. 12 shows the results of experiments showing increased pericyte proliferation/survival when Nell-1 is added.
Figure 13:
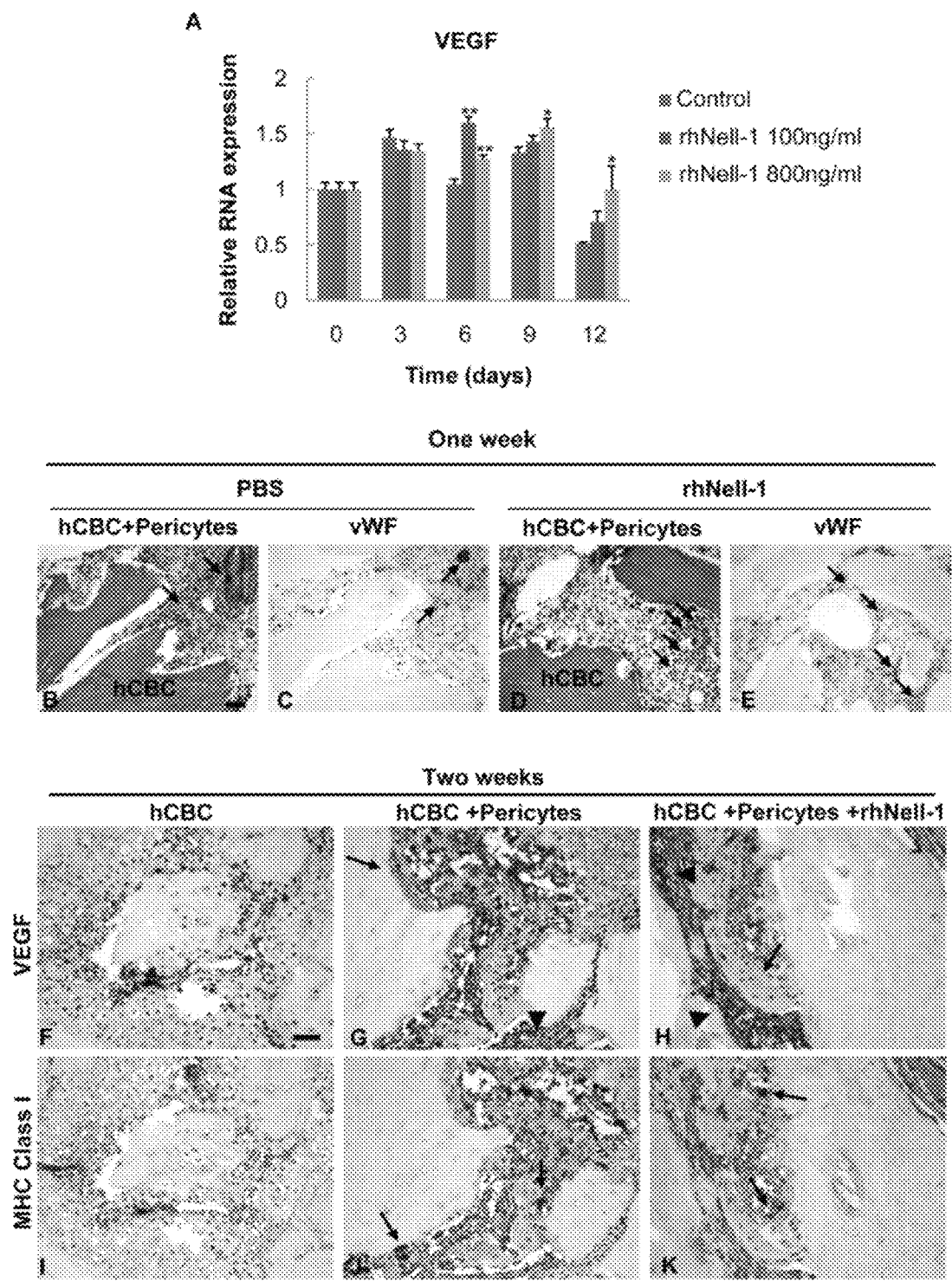
FIG. 13 shows the results of experiments showing increased VEGF expression by pericytes when Nell-1 is added.

Experiments on osteogenic ability of pericytes and NELL-1 factor were performed in a SCID mouse thigh muscle implantation model. The results are shown in FIGS. 12 and 13. FIG. 12 shows increased pericyte proliferation/survival when Nell-1 is added. FIG. 13 shows increased VEGF expression by pericytes when Nell-1 is added.

The above results clearly documented the osteogenic ability of pericytes and NELL-1. These experiments demonstrate the effects of NELL-1 for enhancing survivability and engraftment of PSC or iPS and for causing PSC or iPS to differentiate into osteoblasts or progenitor cell lineage so as to generate a bone tissue.

While particular embodiments of the present invention have been shown and described, it is obvious to those skilled in the art that changes and modifications can be made without departing from this invention in its broader aspects. Therefore, the appended claims are to encompass within their scope all such changes and modifications as fall within the true spirit and scope of this invention.

REFERENCES

1. Giannoudis, P. V. et al. Bone substitutes: an update. Injury 36 Suppl 3, S20-7 (2005).
2. Moerman, E. J. et al. Aging activates adipogenic and suppresses osteogenic programs in mesenchymal marrow stroma/stem cells: the role of PPAR-gamma2 transcription factor and TGF-beta/BMP signaling pathways. Aging Cell 3, 379-89 (2004).
3. Giannoudis, P. et al. Fracture healing in osteoporotic fractures: is it really different? A basic science perspective. Injury 38 Suppl 1, S90-9 (2007).
4. Cornell, C. N. Internal fracture fixation in patients with osteoporosis. J Am Acad Orthop Surg 11, 109-19 (2003).
5. Fernando, T. L. et al. Complete pelvic ring failure after posterior iliac bone graft harvesting. Spine 24, 2101-4 (1999).
6. Rodriguez, J. P. et al. Involvement of adipogenic potential of human bone marrow mesenchymal stem cells (MSCs) in osteoporosis. Curr Stem Cell Res Ther 3, 208-18 (2008).
7. Bueno, E. M. & Glowacki, J. Cell-free and cell-based approaches for bone regeneration. Nat Rev Rheumatol 5, 685-97 (2009).
8. Schultz, D. FDA Public Health Notification: Life-threatening Complications Associated with Recombinant Human Bone Morphogenetic Protein in Cervical Spine Fusion. (ed. Health, C.f.D.a.R.) (2008).
9. Kaneko, H. et al. Direct stimulation of osteoclastic bone resorption by bone morphogenetic protein (BMP)-2 and expression of BMP receptors in mature osteoclasts. Bone 27, 479-86 (2000).
10. Jeppsson, C. & Aspenberg, P. BMP-2 can inhibit bone healing. Bone-chamber study in rabbits. Acta Orthop Scand 67, 589-92 (1996).
11. Aghaloo, T. et al. A study of the role of nell-1 gene modified goat bone marrow stromal cells in promoting new bone formation. Mol Ther 15, 1872-80 (2007).
12. Luo, X. et al. Osteogenic BMPs promote tumor growth of human osteosarcomas that harbor differentiation defects. Lab Invest 88, 1264-77 (2008).

13. Agarwal, R. et al. Osteoinductive bone graft substitutes for lumbar fusion: a systematic review. J Neurosurg Spine 11, 729-40 (2009).
14. Cancedda, R. et al. A tissue engineering approach to bone repair in large animal models and in clinical practice. Biomaterials 28, 4240-50 (2007).
15. Meliga, E. et al. Adipose-derived cells. Cell Transplant 16, 963-70 (2007).
16. Rosland, G. V. et al. Long-term cultures of bone marrow-derived human mesenchymal stem cells frequently undergo spontaneous malignant transformation. Cancer Res 69, 5331-9 (2009).
17. Gad, S. C. Pharmaceutical manufacturing handbook: regulations and quality, p. (John Wiley & Sons, Hoboken, N.J., 2008).
18. Dahl, J. A. et al. Genetic and epigenetic instability of human bone marrow mesenchymal stem cells expanded in autologous serum or fetal bovine serum. Int J Dev Biol 52, 1033-42 (2008).
19. Rajashekhar, G. et al. IFATS collection: Adipose stromal cell differentiation is reduced by endothelial cell contact and paracrine communication: role of canonical Wnt signaling. Stem Cells 26, 2674-81 (2008).
20. Meury, T. et al. Human endothelial cells inhibit BMSC differentiation into mature osteoblasts in vitro by interfering with osterix expression. J Cell Biochem 98, 992-1006 (2006).
21. Hsu, W. K. et al. Stem cells from human fat as cellular delivery vehicles in an athymic rat posterolateral spine fusion model. J Bone Joint Surg Am 90, 1043-52 (2008).
22. Meijer, G. J. et al. Cell-based bone tissue engineering. PLoS Med 4, e9 (2007).
23. Tseng, S. S. et al. Nonunions and the potential of stem cells in fracture-healing. J Bone Joint Surg Am 90 Suppl 1, 92-8 (2008).
24. Chidgey, A. P. et al. Tolerance strategies for stem-cell-based therapies. Nature 453, 330-7 (2008).
25. Grinnemo, K. H. et al. Immunogenicity of human embryonic stem cells. Cell Tissue Res 331, 67-78 (2008).
26. De Ugarte, D. A. et al. Comparison of multi-lineage cells from human adipose tissue and bone marrow. Cells Tissues Organs 174, 101-9 (2003).
27. Aust, L. et al. Yield of human adipose-derived adult stem cells from liposuction aspirates. Cytotherapy 6, 7-14 (2004).
28. Caplan, A. I. The mesengenic process. Clin Plast Surg 21, 429-35 (1994).
29. Chen, C. W. et al. Perivascular multilineage progenitor cells in human organs: Regenerative units, cytokine sources, or both? Cytokines and Growth Factors Reviews (in press) (2009).
30. Zuk, P. A. The Adipose-derived Stem Cell: Looking Back and Looking Ahead. Mol Biol Cell (2010).
31. Cheung, W. K. et al. Osteogenic comparison of expanded and uncultured adipose stromal cells. Cytotherapy (2010).
32. Muller, A. M. et al. Towards an intraoperative engineering of osteogenic and vasculogenic grafts from the stromal vascular fraction of human adipose tissue. Eur Cell Mater 19, 127-35 (2010).
33. Garcia-Olmo, D. et al. Treatment of enterocutaneous fistula in Crohn's Disease with adipose-derived stem cells: a comparison of protocols with and without cell expansion. Int J Colorectal Dis 24, 27-30 (2009).
34. Faustini, M. et al. Non expanded mesenchymal stem cells for regenerative medicine: yield in stromal vascular fraction from adipose tissues. Tissue Eng Part C Methods.
35. Jurgens, W. J. et al. Effect of tissue-harvesting site on yield of stem cells derived from adipose tissue: implications for cell-based therapies. Cell Tissue Res 332, 415-26 (2008).
36. Crisan, M. et al. A perivascular origin for mesenchymal stem cells in multiple human organs. Cell Stem Cell 3, 301-13 (2008).
37. Bagaria, V. & Prasada, V. Bone morphogenic protein: Current state of field and the road ahead. in J. Orthopaedics Vol. 2 e3 (2005).
38. Boraiah, S. et al. Complications of recombinant human BMP-2 for treating complex tibial plateau fractures: a preliminary report. Clin Orthop Relat Res 467, 3257-62 (2009).
39. Irie, K. et al. Osteoclast differentiation in ectopic bone formation induced by recombinant human bone morphogenetic protein 2 (rhBMP-2). J Bone Miner Metab 21, 363-9 (2003).
40. Osyczka, A. M. et al. Different effects of BMP-2 on marrow stromal cells from human and rat bone. Cells Tissues Organs 176, 109-19 (2004).
41. Minear, S. et al. rBMP represses Wnt signaling and influences skeletal progenitor cell fate specification during bone repair. J Bone Miner Res (2010).
42. Takada, I. et al. Wnt and PPARgamma signaling in osteoblastogenesis and adipogenesis. Nat Rev Rheumatol 5, 442-7 (2009).
43. Kang, Q. et al. A comprehensive analysis of the dual roles of BMPs in regulating adipogenic and osteogenic differentiation of mesenchymal progenitor cells. Stem Cells Dev 18, 545-59 (2009).
44. Hata, K. et al. Differential roles of Smad1 and p38 kinase in regulation of peroxisome proliferator-activating receptor gamma during bone morphogenetic protein 2-induced adipogenesis. Mol Biol Cell 14, 545-55 (2003).
45. Jin, W. et al. Schnurri-2 controls BMP-dependent adipogenesis via interaction with Smad proteins. Dev Cell 10, 461-71 (2006).
46. Sottile, V. & Seuwen, K. Bone morphogenetic protein-2 stimulates adipogenic differentiation of mesenchymal precursor cells in synergy with BRL 49653 (rosiglitazone). FEBS Lett 475, 201-4 (2000).
47. Minear, S. et al. Wnt proteins promote bone regeneration. Sci Transl Med 2, 29ra30 (2010).
48. Bokui, N. et al. Involvement of MAPK signaling molecules and Runx2 in the NELL 1-induced osteoblastic differentiation. FEBS Lett 582, 365-71 (2008).
49. Aghaloo, T. et al. A study of the role of nell-1 gene modified goat bone marrow stromal cells in promoting new bone formation. Mol Ther 15, 1872-80 (2007).
50. Cowan, C. M. et al. Synergistic effects of Nell-1 and BMP-2 on the osteogenic differentiation of myoblasts. J Bone Miner Res 22, 918-30 (2007).
51. Zhang, X. et al. Craniosynostosis in transgenic mice overexpressing Nell-1. J Clin Invest 110, 861-70. (2002).
52. Jin, Z. et al. Hypermethylation of the nel-like 1 gene is a common and early event and is associated with poor prognosis in early-stage esophageal adenocarcinoma. Oncogene 26, 6332-40 (2007).
53. Aghaloo, T. et al. Nell-1-induced bone regeneration in calvarial defects. Am J Pathol 169, 903-15 (2006).
54. Cowan, C. M. et al. Nell-1 induced bone formation within the distracted intermaxillary suture. Bone 38, 48-58 (2006).
55. Lu, S. S. et al. The osteoinductive properties of Nell-1 in a rat spinal fusion model. Spine J 7, 50-60 (2007).

56. Lu, S. et al. Nell-1 promotes bone formation in a sheep spinal fusion model. JBMR 22, S171 (2007).
57. Desai, J. et al. Neill-deficient mice have reduced expression of extracellular matrix proteins causing cranial and vertebral defects. Hum Mol Genet. 15, 1329-41 (2006).
58. Siu, R. K. et al. Nell-1 deficient mice exhibit abnormal structure in spinal and long bones. ASBMR, S50-51 (2009).
59. Culiat, C. et al. Nell1 protein is critical for the maturation of heart structure and vasculature during mammalian fetal development. PNAS (2010 (in revision)).
60. Lu, C. & Sood, A. K. Role of Pericytes in Angiogenesis. in Cancer Drug Discovery and Development 117-132 (Humana Press, Totowa, N.J., 1999).
61. Yoon, E. et al. In vivo osteogenic potential of human adipose-derived stem cells/poly lactide-co-glycolic acid constructs for bone regeneration in a rat critical-sized calvarial defect model. Tissue Eng 13, 619-27 (2007).
62. Global Spine Fusion Equipment Market 2009-2013 (Infiniti Research Limited, 2010).
63. Riordan, N. H. et al. Non-expanded adipose stromal vascular fraction cell therapy for multiple sclerosis. J Transl Med 7, 29 (2009).
64. Jin, Z. et al. Hypermethylation of the nel-like 1 gene is a common and early event and is associated with poor prognosis in early-stage esophageal adenocarcinoma. Oncogene (2007).
65. Chen, C. W. et al. Perivascular multi-lineage progenitor cells in human organs: regenerative units, cytokine sources or both? Cytokine Growth Factor Rev 20, 429-34 (2009).
66. Truong, T. et al. Craniosynostosis-associated gene nell-1 is regulated by runx2. J Bone Miner Res 22, 7-18 (2007).
67. Duque, G. Bone and fat connection in aging bone. Curr Opin Rheumatol 20, 429-34 (2008).
68. Crisan, M. et al. Purification and culture of human blood vessel-associated progenitor cells. Curr Protoc Stem Cell Biol Chapter 2, Unit 2B 2 1-2B 2 13 (2008).
69. Pittenger, M. F. et al. Multilineage potential of adult human mesenchymal stem cells. Science 284, 143-7 (1999).
70. Zheng, B. et al. Prospective identification of myogenic endothelial cells in human skeletal muscle. Nat Biotechnol 25, 1025-34 (2007).
71. Tolar, J. et al. Sarcoma derived from cultured mesenchymal stem cells. Stem Cells 25, 371-9 (2007).
72. Li, W. et al. Delivery of lyophilized Nell-1 in a rat spinal fusion model. Tissue Eng, (accepted for publication) (2010).
73. Borah, B. et al. Evaluation of Changes in Trabecular Bone Architecture and Mechanical Properties of Minipig Vetebrate by Three-dimensional Magnetic Resonance Microimaging and Finite Element Modeling. JBMR 15, 1786-1797 (2000).
74. Lelovas, P. P. et al. The laboratory rat as an animal model for osteoporosis research. Comp Med 58, 424-30 (2008).
75. Kon, E. et al. Autologous bone marrow stromal cells loaded onto porous hydroxyapatite ceramic accelerate bone repair in critical-size defects of sheep long bones. J Biomed Mater Res 49, 328-37 (2000).
76. Petite, H. et al. Tissue-engineered bone regeneration. Nat Biotechnol 18, 959-63 (2000).
77. Bensaid, W. et al. De novo reconstruction of functional bone by tissue engineering in the metatarsal sheep model. Tissue Eng 11, 814-24 (2005).
78. Zhu, L. et al. Tissue-engineered bone repair of goat-femur defects with osteogenically induced bone marrow stromal cells. Tissue Eng 12, 423-33 (2006).
79. Marcacci, M. et al. Stem cells associated with macroporous bioceramics for long bone repair: 6- to 7-year outcome of a pilot clinical study. Tissue Eng 13, 947-55 (2007).
80. McKay, W. Science-based assessment: Accelerating product development of combination medical devices. in NMAB Roundtable on Biomedical Engineering Materials and Applications (Washington, D.C., 2003).
81. Crisan, M. et al. Purification and long-term culture of multipotent progenitor cells affiliated with the walls of human blood vessels: myoendothelial cells and pericytes. Methods Cell Biol 86, 295-309 (2008).
82. Fraser, J. K. et al. Adipose-derived stem cells. Methods Mol Biol 449, 59-67 (2008).
83. Gronthos, S. et al. The STRO-1+fraction of adult human bone marrow contains the osteogenic precursors. Blood 84, 4164-73 (1994).

We claim:

1. A composition for bone regeneration, comprising:
an isolated population of perivascular stem cells (PSC), and
an osteoinductive agent,
wherein the osteoinductive agent is in a therapeutically effective amount for causing the isolated population of PSC to differentiate in the osteoblast lineage or in a therapeutically effective amount for enhancing the survivability or engraftment of the isolated population of PSC where the PSC provide trophic factors or enhance vascular ingrowth, and
wherein the PSC are selected from the group consisting of adventitial cells showing positive expression of CD34; adventitial cells showing positive expression of CD34 and negative expression of CD146, NG2, PDGF-β, CD45 and CD31; adventitial cells showing positive expression of CD34 and negative expression of CD146, CD45 and CD31; adventitial cells showing positive expression of CD34 and negative expression of CD146 and CD31; and a combination thereof.

2. The composition of claim 1, wherein the osteoinductive agent is a NELL-1 factor.

3. The composition of claim 1, wherein the PSC has a density of about $1 \times 10^4$ to about $1 \times 10^8$ per 1 mL volume of the composition.

4. The composition of claim 1, which is effective for osteoporosis.

5. The composition of claim 1, which is an osteogenic implant.

6. The composition of claim 1, which is an implant for spine fusion.

7. The composition of claim 1, further comprises an excipient.

8. The composition of claim 1, wherein the osteoinductive agent is a NELL-1 factor, and wherein the composition is an osteogenic scaffold.

9. The composition of claim 1, wherein the PSC further comprise pericytes showing positive expression of CD146, NG2, and PDGF-β and negative expression of CD45, CD34 and CD56; pericytes showing positive expression of CD146, NG2, and PDGF-β and negative expression of CD45, CD34 and CD31; or pericytes showing positive expression of CD146 and negative expression of CD45, CD34 and CD31.

10. A method of treating or ameliorating a bone condition, comprising:

administering to a subject a composition according to claim 1.

11. The method of claim 10, wherein the bone condition is a spine condition or osteoporosis.

12. A method of fabricating a composition for bone regeneration, comprising:
providing an osteoinductive agent,
providing an isolated population of perivascular stem cells (PSC), and
forming the composition,
wherein the osteoinductive agent is in a therapeutically effective amount for causing the isolated population of PSC to differentiate in the osteoblast lineage or in a therapeutically effective amount for enhancing the survivability or engraftment of the isolated population of PSC where the PSC provide trophic factors or enhance vascular ingrowth, and
wherein the PSC are selected from the group consisting of adventitial cells showing positive expression of CD34; adventitial cells showing positive expression of CD34 and negative expression of CD146, NG2, PDGF-β, CD45 and CD31; adventitial cells showing positive expression of CD34 and negative expression of CD146, CD45 and CD31; adventitial cells showing positive expression of CD34 and negative expression of CD146 and CD31; and a combination thereof.

13. The method of claim 12, wherein the osteoinductive agent is a NELL-1 factor.

14. The method of claim 12, wherein the PSC has a density of about $1\times10^4$ to about $1\times10^8$ per 1 mL volume of the composition.

15. The method of claim 12, wherein the composition is effective for osteoporosis.

16. The method of claim 12, wherein the composition is an osteogenic implant.

17. The method of claim 12, wherein the composition is an implant for spine fusion.

18. The method of claim 12, wherein the composition further comprises an excipient.

19. The method of claim 12, wherein the osteoinductive agent is a NELL-1 factor, and wherein the composition is an osteogenic scaffold.

20. The method of claim 12, wherein the PSC further comprise pericytes showing positive expression of CD146, NG2, and PDGF-β and negative expression of CD45, CD34 and CD56; pericytes showing positive expression of CD146, NG2, and PDGF-β and negative expression of CD45, CD34 and CD31; or pericytes showing positive expression of CD146 and negative expression of CD45, CD34 and CD31.

* * * * *